US009487824B2

(12) United States Patent
Kutyavin

(10) Patent No.: US 9,487,824 B2
(45) Date of Patent: Nov. 8, 2016

(54) METHODS AND COMPOSITIONS FOR ENRICHMENT OF NUCLEIC ACIDS IN MIXTURES OF HIGHLY HOMOLOGOUS SEQUENCES

(76) Inventor: Igor Kutyavin, Woodinville, WA (US)

(*) Notice: Subject to any disclaimer, the term of this patent is extended or adjusted under 35 U.S.C. 154(b) by 381 days.

(21) Appl. No.: 14/129,268

(22) PCT Filed: Jun. 28, 2012

(86) PCT No.: PCT/US2012/044710
§ 371 (c)(1),
(2), (4) Date: Mar. 25, 2014

(87) PCT Pub. No.: WO2013/003630
PCT Pub. Date: Jan. 3, 2013

(65) Prior Publication Data
US 2014/0206001 A1    Jul. 24, 2014

Related U.S. Application Data

(60) Provisional application No. 61/502,242, filed on Jun. 28, 2011.

(51) Int. Cl.
*C12Q 1/68* (2006.01)
*C12Q 1/28* (2006.01)

(52) U.S. Cl.
CPC ............. *C12Q 1/6848* (2013.01); *C12Q 1/28* (2013.01); *C12Q 1/6858* (2013.01)

(58) Field of Classification Search
None
See application file for complete search history.

(56) References Cited

U.S. PATENT DOCUMENTS

| | | |
|---|---|---|
| 4,458,066 A | 7/1984 | Caruthers |
| 4,683,195 A | 7/1987 | Mullis |
| 4,683,202 A | 7/1987 | Mullis |
| 5,168,038 A | 12/1992 | Tecott |
| 5,210,015 A | 5/1993 | Gelfand |
| 5,723,591 A | 3/1998 | Livak |
| 5,846,717 A | 12/1998 | Brow |
| 5,854,033 A | 12/1998 | Lizardi |
| 5,985,557 A | 11/1999 | Prudent |
| 5,994,069 A | 11/1999 | Hall |
| 6,063,603 A | 5/2000 | Davey |
| 6,090,543 A | 7/2000 | Prudent |
| 7,381,530 B2 | 6/2008 | Hall |
| 2005/0255512 A1 | 11/2005 | Sorge |
| 2006/0051748 A1 | 3/2006 | Hogrefe |
| 2008/0199916 A1* | 8/2008 | Zheng ............... C12Q 1/6844 435/91.2 |
| 2009/0246788 A1* | 10/2009 | Albert ............... C12Q 1/6827 435/6.12 |
| 2009/0253142 A1* | 10/2009 | Allawi ............... C12Q 1/6827 435/6.1 |
| 2010/0143898 A1* | 6/2010 | Kutyavin ............ C12Q 1/6853 435/6.1 |

FOREIGN PATENT DOCUMENTS

| | | | |
|---|---|---|---|
| AU | WO 9632500 A1 * | 10/1996 | ........... C12Q 1/6858 |
| WO | 2007/127999 A2 | 11/2007 | |

OTHER PUBLICATIONS

International Search Report mailed Jan. 23, 2013, in International Patent Application No. PCT/US2012/044710, filed Jun. 28, 2012, 7 pages.
Afonina, I.A., et al., "Minor Groove Binder-Conjugated DNA Probes for Quantitative DNA Detection by Hybridization-Triggered Fluorescence," Biotechniques 32(4):940-949, Apr. 2002.
An, L., et al., "Characterization of a Thremostable UvrD Helicase and Its Participation in Helicase Dependent Amplification," Journal of Biological Chemistry 280(32):28952-28958, Aug. 12, 2005.
Auer, T., et al., "Selective Amplification of RNA Utilizing the Nucleotide Analog dITP and Thermus Thermophilus DNA Polymerase," Nucleic Acids Research 24(24):5021-5026, 1996.
Ausubel, T., "Hybridization Analysis of DNA Blots," Current Protocols in Molecular Biology vol. 1, Chapter 2, Section I, Supplement 21, John Wiley & Sons, New York, 1993, pp. 2.10.1-2.10.16.
Banér, J., et al., "Signal Amplification of Padlock Probes by Rolling Circle Replication," Nucleic Acids Research 26(22):5073-5078, 1998.
Beaucage, S.L., and M.H. Caruthers, "Deoxynucleoside Phosphoramidites—A New Class of Key Intermediates for Deoxypolynucleotide Synthesis," Tetrahedron Letters 22(20):1859-1862, 1981.
Belyavsky, A., et al., "PCR-Based cDNA Library Construction: General cDNA Libraries at the Level of a Few Cells," Nucleic Acids Research 17(8):2919-2932, 1989.
Bonnet, G., et al., "Thermodynamic Basis of the Enhanced Specificity of Structured DNA Probes," Proceedings of the National Academy of Sciences USA 96:6171-6176, May 1999.
Breslauer, K.J., et al., "Predicting DNA Duplex Stability From the Base Sequence," Proceedings of the National Academy of Sciences USA 83:3746-3750, Jun. 1986.
Cardullo, R.A., et al., "Detection of Nucleic Acid Hybridization by Nonradiative Fluorescence Resonance Energy Transfer," Proceedings of the National Academy of Sciences USA 85:8790-8794, Dec. 1988.

(Continued)

*Primary Examiner* — Angela M Bertagna
(74) *Attorney, Agent, or Firm* — Barry L. Davison; Davis Wright Tremaine LLP

(57) ABSTRACT

Provided are methods of enrichment and detection of target nucleic acids during target amplification in the presence of excess amounts of highly homologous sequences, the methods having substantial diagnostic utility (e.g., cancer diagnostics). Provided are amplification reaction mixtures having at least one cleavage-directing oligonucleotide, the respective binding sites of which, for the target and homologous sequences, include one or more nucleotide positions differing in sequence between the target homologous sequences. During target sequence amplification in the presence of DNA polymerase activity, a FEN1 activity, one or more amplification primers, deoxynucleoside 5'-triphosphates and other reagents suitable to support amplification of both target and homologous nucleic acid sequences, the cleavage directing oligonucleotide hybridizes to the homologous sequence and its amplification products resulting in a FEN1-mediated cleavage of these sequences providing for increased amounts of the target nucleic acid sequence relative to that of the homologous nucleic acid sequences.

21 Claims, 6 Drawing Sheets

(56) References Cited

OTHER PUBLICATIONS

Didenko, V.V., "DNA Probes Using Fluorescence Resonance Energy Transfer," Biotechniques 31(5):1106-1121, Nov. 2001.
Di Giusto, D.A. and G.C. King, "Strong positional preference in the Interaction of LNA Oligonucleotides With DNA Polymerase and Proofreading Exonuclease Activities: Implications for Genotyping Assays," Nucleic Acids Research 32(3):e32, 2004.
Doty, P., et al., "Strand Separation and Specific Recombination in Deoxyribonucleic Acids: Physical Chemical Studies," Proceedings of the National Academy of Sciences USA 46:461-476, 1960.
Eftink, M.R., "Fluorescence Quenching: Theory and Applications," In Lakowicz, J.R. (ed.), Topics in Fluorescence Spectroscopy, Plenum Press, New York, V.2, pp. 53-126, 1991.
Forster, T., "Part III: Action of Light and Organic Crystals," In Sinanoglu, O. (ed.), "Modern Quantum Chemistry, Istanbul Lectures," Academic Press, New York, 1965, pp. 93-137.
Gait, M.J., ed., "Oligonucleotide Synthesis, a Practical Approach," IRL Practical Approach Series, IRL Press, Oxford, Biochemical Education 15(1):52, 1984.
Gocke, C.D., et al., "Enrichment Methods for Mutation Detection," Annals New York Academy of Sciences 9906:31-38, 2000.
Gundry, C.N., et al., "Rapid F508del and F508C Assay Using Fluorescent Hybridization Probes," Genetic Testing 3(4):365-370, 1999.
Hirao, I., et al., "Extraordinarily Stable Mini-Hairpins: Electrophoretical and Thermal Properties of the Various Sequence Variants of d(GCGAAAGC) and Their Effect on DNA Sequencing," Nucleic Acids Research 20(15):3891-3896, 1992.
Kaur, M., et al., "Ligation of a Primer at a Mutation: A Method to Detect Low Level Mutations in DNA," Mutagenesis 17(5):365-373, 2002.
Kutyavin, I.V., "New Approach to Real-Time Nucleic Acids Detection: Folding Polymerase Chain Reaction Amplicons Into a Secondary Structure to Improve Cleavage of Förster Resonance Energy Transfer Probes in 5'-Nuclease Assays," Nucleic Acids Research 38(5)(e29):1-12, 2010.
Kutyavin, I.V., et al., "Oligonucleotides With Conjugated Dihydropyrroloindole Tripeptides: Base Composition and Backbone Effects on Hybridization," Nucleic Acids Research 25(18):3718-3723, 1997.
Kutyavin, I.V., "Use of Base-Modified Duplex-Stablizing Deoxynucleoside 5'-Triphosphates to Enhance the Hybridization Properties of Primers and Probes in Detection Polymerase Chain Reaction," Biochemistry 47(51):13666-13673, 2008.
Jenkins, G.J.S., et al., "Mutation Analysis Using the Restriction Site Mutation (RSM) Assay," Mutation Research 405:209-220, 1998.
Latorra, D., et al., "Design Considerations and Effects of LNA in PCR Primers," Molecular and Cellular Probes 17:253-259, 2003.
Lawyer, F.C., et al., "High-Level Expression, Purification, and Enzymatic Characterization of Full-Length Thermus Aquaticus DNA Polymerase and a Truncated Form Deficient in 5' to 3' Exonuclaese Activity," PCR Methods and Applications 2:275-287, 1993.
Liu, Q., and S.S. Sommer, "Pyrophosphorolysis-Activated Polymerization (PAP): Application to Allele-Specific Amplification," Biotechniques 29:1072-1083, Nov. 2000.
Mackay, I.M., et al., "Real-Time PCR in Virology," Nucleic Acids Research 30(6):1292-1305, 2002.
Mackay, J., and O. Landt, "Real-Time PCR Fluorescent Chemistries," Methods in Molecular Biology 353:237-261, 2007.
Milbury, C.A., et al., "PCR-Based Methods for the Enrichment of Minority Alleles and Mutations," Clinical Chemistry 55(4):632-640, 2009.
Miller, S.A., et al., "A Simple Salting Out Procedure for Extracting DNA From Human Nucleated Cells," Nucleic Acids Research 16(3):1215, 1988.
Oehlenschlager, F., et al., "Detection of HIV-1 RNA by Nucleic Acid Sequence-Based Amplification Combined With Fluorescence Correlation Spectroscopy," Proceedings of the National Academy of Sciences USA, 93:12811-12816, Nov. 1996.
Ortiz, E., et al., "PNA Molecular Beacons for Rapid Detection of PCR Amplicons," Molecular and Cellular Probes 12:219-226, 1998.
Parry, J.M., et al., "Restriction Site Mutation Analysis, a Proposed Methodology for the Detection and Study of DNA Base Changes Following Mutagen Exposure," Mutagenesis 5(3):209-212, 1990.
Parsons, B.L., and R.H. Heflich, "Genotypic Selection Methods for the Direct Analysis of Point Mutations," Mutation Research 387:97-121, 1997.
Puglisi, J.D., and I. Tinoco, Jr., "[22] Absorbance Melting Curves of RNA," Methods in Enzymology 180:304-325, 1989.
Robelek, R., et al., "Multiplexed Hybridization Detection of Quantum Dot-Conjugated DNA Sequences Using Surface Plasmon Enhanced Fluorescence Microscopy and Spectrometry," Analytical Chemistry 76(20):6160-6165, Oct. 15, 2004.
Sambrook J., et al., "Molecular Cloning: A Laboratory Manual," 3rd Edition, Cold Spring Harbor Lab. Cold Spring Harbor, New York, 1989, 21 pages.
Santalucia, Jr., J., "A Unified View of Polymer, Dumbbell, and Oligonucleotide DNA Nearest-Neighbor Thermodynamics," Proceedings of the National Academy of Sciences USA 95:1460-1465, Feb. 1998.
Shi, J., et al., "Detection of Ultrarare Somatic Mutation in the Human TP53 Gene by Bidirectional Pyrophosphorolysis-Activated Polymerization Allele-Specific Amplification," Human Mutation 28(2):131-136, 2007.
Simpson, D., et al., "A Method for Specific Cloning and Sequencing of Human HPRT cDNA for Mutation Analysis," Biochemical and Biophysical Research Communications 151(1):487-492, Feb. 29, 1988.
Stryer, L., and R.P. Haugland, "Energy Transfer: A Spectroscopic Ruler," Proceedings of the National Academy of Sciences USA 58:719-726, 1967.
Sugimoto, N., et al., "Improved Thermodynamic Parameters and Helix Initiation Factor to Predict Stability of DNA Duplexes," Nucleic Acids Research 24(22):4501-4505, 1996.
Thelwell, N., et al., "Mode of Action and Application of Scorpion Primers to Mutation Detection," Nucleic Acids Research 28(19):3752-3761, 2000.
Tyagi, S., and F.R. Kramer, "Molecular Beacons: Probes That Fluoresce Upon Hybridization," Nature Biotechnology 14:303-308, Mar. 1996.
Vincent, M., et al., "Helicase-Dependent Isothermal DNA Amplification," European Molecular Biology Organization (EMBO) Reports 5(8):795-800, 2004.
Walsh, S.P., et al., "Selex® 100 as a Medium for Simple Extraction of DNA for PCR-Based Typing From Forensic Material," Biotechniques 10(4):506-513, 1991.
Whitcombe, D., et al., "Detection of PCR Products Using Self-Probing Amplicons and Fluorescence," Nature Biotechnology 17:804-807, Aug. 1999.
Zhou, L., et al., "Enrichment and Detection of Rare Alleles by Means of Snapback Primers and Rapid-Cycle PCR," Clinical Chemistry 56(5):814-822, 2010.
Zuker, M., and A.B. Jacobsen, "'Well-Determined' Regions in RNA Secondary Structure Prediction: Analysis of Small Subunit Ribosomal RNA," Nucleic Acids Research 23(14):2791-2798, 1995.

* cited by examiner

SEQUENCE LISTING

```
<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: seq id no:1 of fig 4
<220> FEATURE:
<221> NAME/KEY: misc_feature
<222> LOCATION: (3)..(3)
<223> OTHER INFORMATION: inosine at this position
<220> FEATURE:
<221> NAME/KEY: misc_feature
<222> LOCATION: (5)..(5)
<223> OTHER INFORMATION: inosine at this position
<220> FEATURE:
<221> NAME/KEY: misc_feature
<222> LOCATION: (6)..(6)
<223> OTHER INFORMATION: inosine at this position
<220> FEATURE:
<221> NAME/KEY: misc_feature
<222> LOCATION: (11)..(11)
<223> OTHER INFORMATION: inosine at this position
<220> FEATURE:
<221> NAME/KEY: misc_feature
<222> LOCATION: (14)..(14)
<223> OTHER INFORMATION: inosine at this position
<220> FEATURE:
<221> NAME/KEY: misc_feature
<222> LOCATION: (16)..(16)
<223> OTHER INFORMATION: inosine at this position
<220> FEATURE:
<221> NAME/KEY: misc_feature
<222> LOCATION: (18)..(18)
<223> OTHER INFORMATION: inosine at this position

<400> SEQUENCE: 1
ccncnncttc nccncnanaa cac                                              23

<210> SEQ ID NO 2
<211> LENGTH: 23
<212> TYPE: DNA
<213> ORGANISM: Artificial Sequence
<220> FEATURE:
<223> OTHER INFORMATION: seq id no:2 of fig.4

<400> SEQUENCE: 2
gtgttctcgc ggcgaagccg cgg                                              23
```

```
<210> SEQ ID NO 3
<211> LENGTH: 21
<212> TYPE: DNA
<213> ORGANISM: Artificial Sequence
<220> FEATURE:
<223> OTHER INFORMATION: forward primer

<400> SEQUENCE: 3
gcattcctga agctgacagc a                                              21

<210> SEQ ID NO 4
<211> LENGTH: 96
<212> TYPE: DNA
<213> ORGANISM: Artificial Sequence
<220> FEATURE:
<223> OTHER INFORMATION: antisense strand

<400> SEQUENCE: 4
tagcctccag gccagaaaga gagagtagcg cgagcacagc taaggccacg gagcgagaca    60
tctcggcccg aatgctgtca gcttcaggaa tgcccg                              96

<210> SEQ ID NO 5
<211> LENGTH: 36
<212> TYPE: DNA
<213> ORGANISM: Artificial Sequence
<220> FEATURE:
<223> OTHER INFORMATION: CD-ODN2-1
<220> FEATURE:
<221> NAME/KEY: misc_feature
<222> LOCATION: (1)..(1)
<223> OTHER INFORMATION: modified with 5' BHQ1quencher

<400> SEQUENCE: 5
gccgagatgt ctcgctccgc ccgcggaacg cgggca                              36

<210> SEQ ID NO 6
<211> LENGTH: 36
<212> TYPE: DNA
<213> ORGANISM: Artificial Sequence
<220> FEATURE:
<223> OTHER INFORMATION: CD-ODN2-2
<220> FEATURE:
<221> NAME/KEY: misc_feature
<222> LOCATION: (1)..(1)
<223> OTHER INFORMATION: modified with 5' BHQ1quencher
<220> FEATURE:
<221> NAME/KEY: misc_feature
<222> LOCATION: (1)..(1)
<223> OTHER INFORMATION: 2'-O-methyl riboguanosine (2'-meG)
<220> FEATURE:
<221> NAME/KEY: misc_feature
<222> LOCATION: (2)..(2)
<223> OTHER INFORMATION: 5-methyl 2'-O-methyl ribocytidine (2'-me 5-meC)
<220> FEATURE:
<221> NAME/KEY: misc_feature
<222> LOCATION: (3)..(3)
<223> OTHER INFORMATION: 5-methyl 2'-O-methyl ribocytidine (2'-me 5-meC)
<220> FEATURE:
<221> NAME/KEY: misc_feature
<222> LOCATION: (4)..(4)
<223> OTHER INFORMATION: 2'-O-methyl riboguanosine (2'-meG)

<400> SEQUENCE: 6
gccgagatgt ctcgctccgc ccgcggaacg cgggca                              36

<210> SEQ ID NO 7
<211> LENGTH: 36
<212> TYPE: DNA
```

<213> ORGANISM: Artificial Sequence
<220> FEATURE:
<223> OTHER INFORMATION: CD-ODN2-3
<220> FEATURE:
<221> NAME/KEY: misc_feature
<222> LOCATION: (1)..(1)
<223> OTHER INFORMATION: modified with 5' BHQ1quencher
<220> FEATURE:
<221> NAME/KEY: misc_feature
<222> LOCATION: (1)..(1)
<223> OTHER INFORMATION: 2'-O-methyl riboguanosine (2'-meG)
<220> FEATURE:
<221> NAME/KEY: misc_feature
<222> LOCATION: (2)..(2)
<223> OTHER INFORMATION: 5-methyl 2'-O-methyl ribocytidine (2'-me 5-meC)
<220> FEATURE:
<221> NAME/KEY: misc_feature
<222> LOCATION: (3)..(3)
<223> OTHER INFORMATION: 5-methyl 2'-O-methyl ribocytidine (2'-me 5-meC)
<220> FEATURE:
<221> NAME/KEY: misc_feature
<222> LOCATION: (4)..(4)
<223> OTHER INFORMATION: 2'-O-methyl riboguanosine (2'-meG)
<220> FEATURE:
<221> NAME/KEY: misc_feature
<222> LOCATION: (5)..(5)
<223> OTHER INFORMATION: 2'-O-methyl riboadenosine analog (2'-meA)
<220> FEATURE:
<221> NAME/KEY: misc_feature
<222> LOCATION: (6)..(5)
<223> OTHER INFORMATION: 2'-O-methyl riboguanosine (2'-meG)
<220> FEATURE:
<221> NAME/KEY: misc_feature
<222> LOCATION: (7)..(7)
<223> OTHER INFORMATION: 2'-O-methyl riboadenosine analog (2'-meA)
<220> FEATURE:
<221> NAME/KEY: misc_feature
<222> LOCATION: (8)..(8)
<223> OTHER INFORMATION: 2'-O-methyl ribothymidine  (2'-meT)

<400> SEQUENCE: 7
gccgagatgt ctcgctccgc ccgcggaacg cgggca                      36

<210> SEQ ID NO 8
<211> LENGTH: 36
<212> TYPE: DNA
<213> ORGANISM: Artificial Sequence
<220> FEATURE:
<223> OTHER INFORMATION: CD-ODN1-3
<220> FEATURE:
<221> NAME/KEY: misc_feature
<222> LOCATION: (1)..(1)
<223> OTHER INFORMATION: modified with 5' BHQ1quencher
<220> FEATURE:
<221> NAME/KEY: misc_feature
<222> LOCATION: (1)..(1)
<223> OTHER INFORMATION: 5-methyl 2'-O-methyl ribocytidine (2'-me 5-meC)
<220> FEATURE:
<221> NAME/KEY: misc_feature
<222> LOCATION: (2)..(2)
<223> OTHER INFORMATION: 2'-O-methyl riboadenosine analog (2'-meA)
<220> FEATURE:
<221> NAME/KEY: misc_feature
<222> LOCATION: (3)..(3)
<223> OTHER INFORMATION: 5-methyl 2'-O-methyl ribocytidine (2'-me 5-meC)
<220> FEATURE:
<221> NAME/KEY: misc_feature
<222> LOCATION: (4)..(4)
<223> OTHER INFORMATION: 2'-O-methyl riboadenosine analog (2'-meA)
<220> FEATURE:
<221> NAME/KEY: misc_feature
<222> LOCATION: (5)..(5)
<223> OTHER INFORMATION: 2'-O-methyl riboguanosine (2'-meG)
<220> FEATURE:
<221> NAME/KEY: misc_feature
<222> LOCATION: (6)..(6)
<223> OTHER INFORMATION: 5-methyl 2'-O-methyl ribocytidine (2'-me 5-meC)

```
<220> FEATURE:
<221> NAME/KEY: misc_feature
<222> LOCATION: (7)..(7)
<223> OTHER INFORMATION: 2'-O-methyl ribothymidine (2'-meT)
<220> FEATURE:
<221> NAME/KEY: misc_feature
<222> LOCATION: (8)..(8)
<223> OTHER INFORMATION: 2'-O-methyl riboadenosine analog (2'-meA)

<400> SEQUENCE: 8
cacagctaag gccacggagc ccgcggaacg cgggca                              36

<210> SEQ ID NO 9
<211> LENGTH: 36
<212> TYPE: DNA
<213> ORGANISM: Artificial Sequence
<220> FEATURE:
<223> OTHER INFORMATION: CD-ODN1-2
<220> FEATURE:
<221> NAME/KEY: misc_feature
<222> LOCATION: (1)..(1)
<223> OTHER INFORMATION: modified with 5' BHQ1quencher
<220> FEATURE:
<221> NAME/KEY: misc_feature
<222> LOCATION: (1)..(1)
<223> OTHER INFORMATION: 5-methyl 2'-O-methyl ribocytidine (2'-me 5-meC)
<220> FEATURE:
<221> NAME/KEY: misc_feature
<222> LOCATION: (2)..(2)
<223> OTHER INFORMATION: 2'-O-methyl riboadenosine analog (2'-meA)
<220> FEATURE:
<221> NAME/KEY: misc_feature
<222> LOCATION: (3)..(3)
<223> OTHER INFORMATION: 5-methyl 2'-O-methyl ribocytidine (2'-me 5-meC)
<220> FEATURE:
<221> NAME/KEY: misc_feature
<222> LOCATION: (4)..(4)
<223> OTHER INFORMATION: 2'-O-methyl riboadenosine analog (2'-meA)

<400> SEQUENCE: 9
cacagctaag gccacggagc ccgcggaacg cgggca                              36

<210> SEQ ID NO 10
<211> LENGTH: 36
<212> TYPE: DNA
<213> ORGANISM: Artificial Sequence
<220> FEATURE:
<223> OTHER INFORMATION: CD-ODN1-1
<220> FEATURE:
<221> NAME/KEY: misc_feature
<222> LOCATION: (1)..(1)
<223> OTHER INFORMATION: modified with 5' BHQ1quencher

<400> SEQUENCE: 10
cacagctaag gccacggagc ccgcggaacg cgggca                              36

<210> SEQ ID NO 11
<211> LENGTH: 96
<212> TYPE: DNA
<213> ORGANISM: Artificial Sequence
<220> FEATURE:
<223> OTHER INFORMATION: sense strand

<400> SEQUENCE: 11
cgggcattcc tgaagctgac agcattcggg ccgagatgtc tcgctccgtg gccttagctg    60
tgctcgcgct actctctctt tctggcctgg aggcta                             96

<210> SEQ ID NO 12
<211> LENGTH: 24
<212> TYPE: DNA
```

```
<213> ORGANISM: Artificial Sequence
<220> FEATURE:
<223> OTHER INFORMATION: reverse primer

<400> SEQUENCE: 12
ctccaggcca gaaagagaga gtag                                              24
```

METHODS AND COMPOSITIONS FOR ENRICHMENT OF NUCLEIC ACIDS IN MIXTURES OF HIGHLY HOMOLOGOUS SEQUENCES

CROSS-REFERENCE TO RELATED APPLICATIONS

This application is the United States national phase, under 35 U.S.C. §371, of International Patent Application No. PCT/US2012/044710, filed 28 Jun. 2012 and entitled METHODS AND COMPOSITIONS FOR ENRICHMENT OF NUCLEIC ACIDS IN MIXTURES OF HIGHLY HOMOLOGOUS SEQUENCES, which claims the benefit of priority to U.S. Provisional Patent Application Ser. No. 61/502,242, filed 28 Jun. 2011 and entitled METHODS AND COMPOSITIONS FOR ENRICHMENT OF NUCLEIC ACIDS IN MIXTURES OF HIGHLY HOMOLOGOUS SEQUENCES, both of which are incorporated herein by reference in their entirety.

CROSS-REFERENCE TO RELATED APPLICATIONS

This application claims the benefit of priority to U.S. Provisional Patent Application Ser. No. 61/502,242, filed 28 Jun. 2011, which is incorporated herein by reference in its entirety.

FIELD OF THE INVENTION

Aspects of the invention relate generally to methods of enrichment and detection of target nucleic acids during target amplification in the presence of excess amounts of highly homologous sequences to provide for preferential amplification and increase in the amount of the target nucleic acid relative to that of the homologous nucleic acid. Particular aspects relate to diagnostics methods and compositions, which have substantial diagnostic utility, including but not limited to cancer diagnostics.

SEQUENCE LISTING

A Sequence Listing, comprising 12 SEQ ID NOS, has been provided in computer readable form (.txt) as part of this application, and is incorporated by reference herein in its entirety.

BACKGROUND

The ability to discern mutations is important in many ways, but is especially important for cancer research and clinical diagnostics. Certain polymorphic variations in nucleic acid sequences, commonly as small as single nucleotide polymorphism (SNP), serve as markers of cancer development and progression. Identification and detection of these sequence variations enables early cancer detection from tissue biopsies and body fluids such as plasma or serum; assessment of residual disease after radio- and chemotherapy; disease staging and molecular profiling for prognosis or tailoring therapy to individual patients; and monitoring of the therapy outcome and cancer remission. The first problem of cancer diagnostics is that the DNA or RNA prognostic markers are usually present in very limited amounts, commonly less than <1,000 molecules per sample. Quantitative and accurate detection of these marker loads remains challenging even though, in theory, certain DNA amplification protocols including Polymerase Chain Reaction (PCR) can quickly increase the target concentration to a detectable level from as little as a single DNA molecule. The main challenge of cancer diagnostics, however, is that the clinical samples are typically composed of both normal (wild-type) and mutant DNAs, and the quantity of normal DNA often vastly exceeds the mutant loads, making it very difficult to detect and identify the minority alleles. This means that, in order to be used as a routing tool, any particular method in cancer diagnostics has to be both highly sensitive and exceptionally sequence-specific. An ideal assay should be fast (real-time), cost-effective, simple to use, and capable of detecting limited amounts of mutant alleles (1-100 copies) in the presence of $10^5$-$10^6$ times excess of normal gene sequences. More than a dozen of different methods have been developed and tested to date (Gocke C. D. et al, 2000; Milbury C. A. et al, 2009; Parsons B. L., Heflich R. H., 1997; Zhou L. et al., 2010).

Despite the considerable progress achieved, the main problem has not yet been solved and the ideal mutant-enriching remains to be developed. The majority of the developed methods exhibit insufficient mutant-enrichment power ($10^2$-$10^3$). In cases where excellent mutant-enrichment is achieved, a particular assay is either too complex or multistage like APRIL-ATM (Kaur M. et al, 2002) and difficult to automate. The bi-PAP-ASA technology (Liu Q., Sommer S. S., 2000; Shi J. et al, 2007) provides limited capabilities to adapt probe-based detection. The RFLP-PCR assay family (Parry J. M. et al, 1990; Jenkins G. J. S. et al, 1998) is very powerful in mutant enrichment but these technologies are generally limited to the mutations located in restriction nucleases' sites while all other sequences are not covered. There is therefore a pronounced need in the art for more efficient and versatile methods of nucleic acids detection that can provide an exceptionally high level of mutant allele enrichment, up to $10^6$ or more, and identify the target sequence variation as small as SNP regardless of the polymorphism, its target location and surrounding sequence contents.

DETAILED DESCRIPTION OF EXEMPLARY EMBODIMENTS

Definitions

Figure 1:
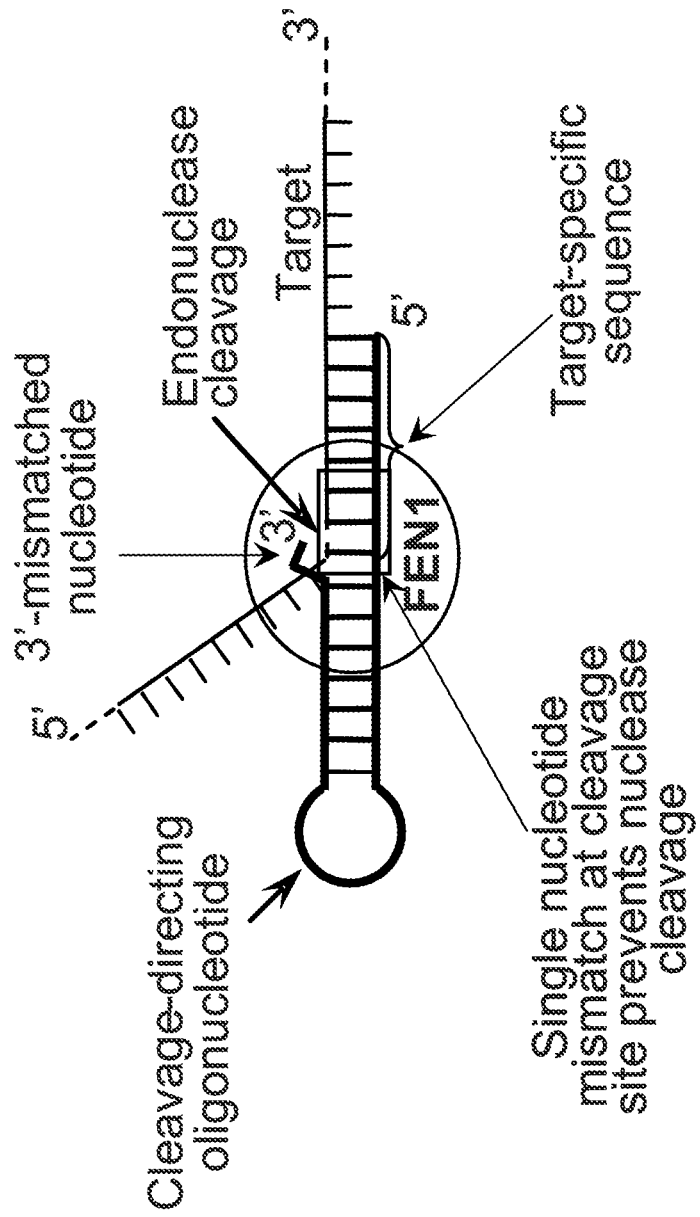
FIG. 1 illustrates the system design which enables cleavage of a single-stranded DNA at any nucleotide position using a cleavage-directing oligonucleotide. The FEN1 nuclease substrate in this design is a simulated or pseudo nicked double-stranded DNA. In the optimal cleavage substrate, the duplexes on each side of the nick are in coaxial stacking with no unpaired nucleotides between them. Appearance of the unpaired nucleotides between the duplexes negatively affects the FEN1 cleavage. Both 5' and 3'-ends of the DNA strand at the site of the nick may or may not have flap-sequences.

Terms and symbols of biochemistry, nucleic acid chemistry, molecular biology and molecular genetics used herein follow those of standard treaties and texts in the field (e.g., Sambrook J. et al, 1989; Kornberg A. and Baker T., 1992; Gait M. J., ed., 1984; Lehninger A. L., 1975; Eckstein F., ed., 1991, and the like). To facilitate understanding of particular exemplary aspects of the invention, a number of terms are discussed below.

In particular aspects, "sample" refers to any substance containing or presumed to contain a nucleic acid of interest. The term "sample" thus includes but is not limited to a sample of nucleic acid, cell, organism, tissue, fluid, for example, spinal fluid or lymph fluid, or substance including but not limited to, for example, plasma, serum, urine, tears, stool, respiratory and genitourinary tracts, saliva, semen, fragments of different organs, tissue, blood cells, samples of in vitro cell cultures, isolates from natural sources such as drinking water, microbial specimens, and objects or specimens that have been suspected to contain nucleic acid molecules.

In particular aspects, "target nucleic acid" or "nucleic acid of interest" refers to a nucleic acid or a fragment of nucleic that is to be amplified, enriched and/or detected using methods of the present invention. Nucleic acids of interest can be of any size and sequence; e.g. as big as genomic DNA. Preferably, the nucleic acid is of a size that provides for detection, enrichment and/or amplification thereof. Two or more target nucleic acids can be fragments or portions of the same nucleic acid molecule. As used herein, nucleic acids are different if they differ in nucleotide sequence by at least one nucleotide. In this aspect, the terms "homology" and "homologous" are used to describe a degree of identity between nucleic acids. There may be partial, low, high, or complete homology. The invention may be used to amplify, enrich and detect "polymorphic variations" or "nucleotide sequence variations" wherein, for example, two nucleic acids of interest have significant degree of identity (homology) in the sequence but differ by only a few nucleotides (e.g. insertions, deletions) or by a single nucleotide, or single nucleotide polymorphism (SNP). Target nucleic acids can be single-stranded or double-stranded. When nucleic acid of interest is double-stranded or presumed to be double-stranded, the term "target nucleic acid" refers to a specific sequence in either strand of double-stranded nucleic acid. Therefore the full complement to any single stranded nucleic acid of interest is treated herein as the same (or complementary) target nucleic acid. In certain aspects, target nucleic acids of the invention comprise polynucleotides comprising natural and/or modified nucleotides, if presence of these structural modifications is beneficial for the methods of the invention, e.g. duplex-stabilizing base-modified nucleotide to enhance hybridization properties of primers, cleavage-directing oligonucleotides and probes.

In particular aspects, "amplification" and "amplifying" target nucleic acids, in general, refers to a procedure wherein multiple copies of the nucleic acid of interest are generated in the form of DNA copies. The term "preferential amplification" is usually applied herein to a target nucleic acid and it refers to a situation wherein the DNA replication yield of the nucleic acid of interest is greater than that for a homologous nucleic acid during the amplification.

The term "enrichment" refers to a process wherein amount of a nucleic acid is increased relative to amount of another, usually homologous nucleic acid. In this aspect, the enrichment can be measured using a simple formula of $E(n) = C_{targ}^{n} \cdot C_{hom}^{0} / C_{hom}^{n} \cdot C_{targ}^{0}$ wherein $E(n)$ is the enrichment factor at any given amplification stage (e.g. PCR cycle n), and $C_{targ}$ and $C_{hom}$ are respectively the concentrations or amounts of the target (targ) and homologous (hom) nucleic acids in the reaction mixture before ($C^0$) and at any given amplification stage (e.g. PCR cycle n ($C^n$)). When it is said herein that the methods of the invention provides, for example, 1000 times enrichment, this means that E=1000 at the end of the amplification. In the methods of the invention the enrichment is achieved by selective cleavage of a homologous sequence during the amplification reaction. The cleavage leads to the reduction of the amplification yield and usually observed as a suppression of the homologous sequence amplification. In this aspect, the terms "enrichment" and "suppression" relate to the same phenomenon and may be used herein interchangeably.

In particular aspects, "amplicon" or "amplification product" refers to a primer extension product or products of amplification that may be a population of polynucleotides, single- or double-stranded, that are replicated from either strand or from one or more nucleic acids. Regardless of the originating nucleic acid strand and the amplicons state, e.g. double- or single-stranded, all amplicons which are usually homologous are treated herein as amplification products of the same nucleic acid including the products of incomplete extension.

In particular aspects, the terms "complementary" or "complementarity" are used herein in reference to the polynucleotides base-pairing rules. Double-stranded DNA, for example, consists of base pairs wherein, for example, G forms a three hydrogen bond couple, or pairs with C, and A forms a two hydrogen bond complex, or pairs with T, and it is regarded that G is complementary to C, and A is complementary to T. In this sense, for example, an oligonucleotide 5'-GATTTC-3' is complementary to the sequence 3'-CTAAAG-5'. Complementarity may be "partial" or "complete." For example, as referred to herein the term "complementary" incorporates both partial and complete complementarity. In partial complementarity, only some of the nucleic acids bases are matched according to the base pairing rules. The degree of complementarity between nucleic acid strands has significant effects on the strength of hybridization between nucleic acids. This is particularly important in performing amplification, enrichment and detection reactions that depend upon nucleic acids binding. The terms may also be used in reference to individual nucleotides and oligonucleotide sequences within the context of polynucleotides. As used herein, the terms "complementary" or "complementarity" refer to the most common type of complementarity in nucleic acids, namely Watson-Crick base pairing as described above, although the oligonucleotide components and amplification products of the invention may participate, including an intelligent design, in other types of "non-canonical" pairings like Hoogsteen, wobble and G-T mismatch pairing.

In particular aspects, the term "secondary structure" refers to an intermolecular complex formation of one sequence in a polynucleotide with another sequence in the same polynucleotide due to complete or partial complementarity between these two sequences. Unless specified otherwise, the term "complex" means the same as "duplex" and it represents a double-stranded fragment or portion of a nucleic acid formed on the principal rules of the Watson-Crick base pairing. The terms "hairpin" structure or "stem-loop" structure may be also used herein describing elements of secondary structure and both terms refer to a double-helical region (stem) formed by base pairing between complementary sequences in a single strand RNA or DNA. "Snake technology" is a nucleic acids detection method which particularly relies on PCR amplicons to fold into secondary structures (Kutyavin I. V., 2010).

"PCR" is an abbreviation of term "polymerase chain reaction," the art-recognized nucleic acid amplification technology (e.g., U.S. Pat. Nos. 4,683,195 and 4,683,202 to Mullis K. B.). The commonly used PCR protocol employs two oligonucleotide primers, one for each strand, designed such that extension of one primer provides a template for the other primer in the next PCR cycle. Generally, a PCR reaction consists of repetitions (or cycles) of (i) a denaturation step which separates the strands of a double-stranded nucleic acid, followed by (ii) an annealing step, which allows primers to anneal to positions flanking a sequence of interest, and then (iii) an extension step which extends the primers in a 5' to 3' direction, thereby forming a nucleic acid fragment complementary to the amplified sequence. Each of the above steps may be conducted at a different temperature using an automated thermocycler. The PCR cycles can be repeated as often as desired resulting in an exponential accumulation of a DNA amplicon fragment whose termini are usually defined by the 5'-ends of the primers used. Particular temperatures, incubation times at each step and rates of change between steps depend on many factors well-known to those of ordinary skill in the art and the examples can be found in numerous published protocols (e.g., McPherson M. J. et al., 1991 and 1995; and the like). Although conditions of PCR can vary in a broad range, a double-stranded target nucleic acid is usually denatured at a temperature of >90° C., primers are annealed at a temperature in the range of about 50-75° C., and the extension is preferably performed in the 72-75° C. range. The term "PCR" encompasses numerous derivative forms of the reaction, including but not limited to, "RT-PCR," "real-time PCR," "nested PCR," "quantitative PCR," "multiplexed PCR," "asymmetric PCR" and the like.

As used herein, the term "nuclease" refers to an enzyme which expresses a phosphomonoesterase or phosphodiesterase activity and capable of cleaving a phosphorester bond in compounds such as R'—O—P(O)(OH)$_2$ and R'—O—P(O)(OH)—O—R" resulting in products R'—OH+P(O)(OH)$_3$ and R'—OH+P(O)(OH)$_2$—O—R" (or R"—OH+P(O)(OH)$_2$—O—R'), respectively and wherein R' and R" may be moieties of any structure which are not necessarily of a nucleotide nature. The term "nucleases" incorporates both "exo" and "endo" nucleases.

The term "duplex-specific nuclease activity" refers to enzymes that recognize specific DNA duplex structures and cleave these structures. The duplex-specific nucleases do not substantially cleave oligonucleotides or polynucleotides when they are in a single stranded state.

The terms "5'-nuclease", "5'-flap endonuclease", "flap endonuclease", "FEN" and "FEN1" refers to duplex-specific nucleases that preferentially cleaves, e.g., the exemplary structure illustrated in FIG. 1. Duplex-specific 5'-nuclease activities useful in practicing the invention may be found in many DNA polymerases, e.g. *E. coli* DNA polymerase I and DNA polymerase isolated from *Thermus aquaticus* (Taq), *Thermus thermophilus* (Tth), *Pyrococcus furiosus* (Pfu) and *Thermus flavus* (Tfl). In certain embodiments of the invention, both assay activities, DNA polymerase and 5'-nuclease, are provided by the same enzyme, for example, Taq polymerase. The 5'-nucleases can be enzymes with no associated DNA polymerase activity. The terms "5'-flap endonuclease", "flap endonuclease", "FEN" and "FEN1" are usually used in these cases. Flap endonucleases are a class of nucleolytic enzyme that acts as structure-specific 5'-exo and 5'-endonucleases during DNA replication, DNA repair and DNA recombination. Flap endonucleases have been identified in eukaryotes, prokaryotes, archea and viruses.

In certain preferred embodiments of the present invention, detection of the target nucleic acids can be performed in "real-time" or "real time." Real time detection is possible when all detection components are available during the amplification and the reaction conditions such as temperature, buffering agents to maintain pH at a selected level, salts, co-factors, scavengers, and the like support both stages of the reaction, amplification and the detection. This permits a target nucleic acid to be measured as the amplification reaction progresses decreasing the number of subsequent handling steps required for the detection of amplified material. "Real-time detection" means an amplification reaction for which the amount of reaction product, e.g. target nucleic acid, is monitored as the reaction proceeds. Reviews of the detection chemistries for real-time amplification can be also found in Didenko V. V., 2001, Mackay I. M. et al, 2002, and Mackay J., Landt O., 2007, which are incorporated herein by reference. In preferred embodiments of the present invention, detection of nucleic acids is based on use of FRET effect and FRET probes.

In certain aspects, the amplification/enrichment and detection stages of the invention may be performed separately, not in real time, when the detection stage follows the amplification. The terms "detection performed after the amplification," "target nucleic acid is amplified before the detection reaction" and "post-amplification detection" are used herein to describe such assays.

"Multiplexed amplification" refers to an amplification reaction wherein multiple target nucleic acids are simultaneously amplified. Correspondingly, the terms "multiplexed enrichment" and "multiplexed detection" refers to the enrichment and detection reactions wherein multiple target nucleic acids are simultaneously enriched and detected.

"Polynucleotide" and "oligonucleotide" are used herein interchangeably and each means a linear polymer of nucleotide monomers. Polynucleotides typically range in size from a few monomeric units, e.g. 5-40, when they are usually referred to as "oligonucleotides," to several thousand monomeric units. The exact size will depend on many factors, which in turn depends on the ultimate function or use of the oligonucleotide. The oligonucleotides may be generated in any manner, including chemical synthesis, DNA replication, reverse transcription, or a combination thereof. Whenever a polynucleotide or oligonucleotide is represented by a sequence of letters, for example, "CCGTATG," it is understood herein, unless otherwise specified in the text, that the nucleotides are in 5'→3' order from left to right and that "A" denotes deoxyadenosine, "C" denotes deoxycytidine, "G" denotes deoxyguanosine, and "T" denotes deoxythymidine. Usually DNA polynucleotides comprise these four deoxyribonucleosides linked by phosphodiester linkage whereas RNA comprises uridine ("U") in place of "T" for the ribose counterparts.

The terms "natural nucleosides" and "natural nucleotides" as used herein refer to four deoxynucleosides or deoxynucleotides respectively which may be commonly found in DNAs isolated from natural sources. Natural nucleosides (nucleotides) are deoxyadenosine, deoxycytidine, deoxyguanosine, and deoxythymidine. The term also encompasses their ribose counterparts, with uridine in place of thymidine.

As used herein, the terms "unnatural nucleosides" or "modified nucleosides" refer to nucleotide analogs that are different in their structure from those natural nucleotides for DNA and RNA polymers. The same terms can be used in regard to corresponding nucleotides that also can be "unnatural" or "modified". Some of the naturally occurring nucleic acids of interest may contain nucleosides that are structurally different from the natural nucleosides defined above, for example, DNAs of eukaryotes may incorporate 5-methyl-cytosine and tRNAs are notorious for harboring many nucleoside analogs. However, as used herein, the terms "unnatural nucleosides" or "modified nucleotides" encompasses these nucleoside modifications even though they can be found in natural sources. For example, ribothymidine and deoxyuridine are treated herein as unnatural nucleosides. The modified nucleosides can be "polymerase-efficient" or "polymerase-deficient". The polymerase-efficient nucleoside analogs support the primer extension and DNA replication when they appear in the template strand. Deoxyinosine and deoxyuridine are examples of such polymerase-efficient nucleoside modifications. When these nucleoside modifications are in the template strand, DNA polymerase readily incorporates their Watson-Crick counterparts, correspondingly deoxycytidine and deoxyadenosine. Many structural modifications of a non-nucleoside nature like various chemical linkers are "polymerase-deficient", i.e. do not support the primer extension and terminate DNA synthesis at the site of the modification.

The term "oligonucleotide component" refers to any molecule of polynucleotide nature that is required or helpful in conducting either amplification/enrichment or detection reaction of the invention or both. Oligonucleotide components include but not limited to primers including, cleavage-directing oligonucleotides, probes, hybridization and cleavage enhancers, effectors, etc. Oligonucleotide components can be labeled or have structural modifications of any kind.

As used herein, the term "cleavage-directing" functional activity means capability of an oligonucleotide component to direct a flap endonuclease activity to a specific site (e.g. internucleotide phosphodiester linkage) usually within a homologous nucleic acid. The cleavage-directing oligonucleotide or "CD-oligonucleotide" and "CD-ODN" may provide for the cleavage of the nucleic acid of interest but the efficiency of this cleavage is lower than that for the homologous sequence.

The terms "oligonucleotide primer" and/or "primer" refer to a single-stranded DNA or RNA molecule that hybridizes to a target nucleic acid and primes enzymatic synthesis of a second nucleic acid strand in presence of a DNA polymerase. In this case, as used herein, the target nucleic acid "serves as a template" for the oligonucleotide primer. The term "DNA priming" is used herein to describe the functional activity of oligonucleotide primers.

As used herein, the term an "oligonucleotide probe" or "probe" refers to an oligonucleotide component which is used to detect nucleic acids. These terms encompasses various derivative forms such as, e.g. "hybridization-triggered probe", "cleavable probe", "fluorescent probe", "FRET probe", etc.

The term "structural modifications" refers to any chemical substances such as atoms, moieties, residues, polymers, linkers or nucleotide analogs which are usually of a synthetic nature and which are not commonly present in natural nucleic acids. As used herein, the term "structural modifications" also include nucleoside or nucleotide analogs which rarely present in natural nucleic acid including but not limited to inosine (hypoxanthine), 5-bromouracil, 5-methylcytosine, 5-iodouracil, 2-aminoadenosine, 6-methyladenosine, preudouridine and the like.

"Duplex-stabilizing modifications" refer to structural modifications, the presence of which in double-stranded nucleic acids provides a duplex-stabilizing effect when compared in thermal stability, usually measured as melting temperature (Tm), with respective nucleic acid complexes that have no structural modification and comprised natural nucleotides. Duplex-stabilizing modifications are structural modifications that are most commonly applied in synthesis of probes and primers and represented by modified nucleotides and 'tails' like intercalators and minor groove binders. Certain structural modifications negatively affect the duplex stability, and the term "duplex-destabilizing modifications" is used herein to describe these modifications. For example, the duplex-destabilizing nucleoside modifications such as deoxyinosine and deoxyuridine may be useful in practicing the methods of the invention.

The term "5'-nuclease-protecting modifications" refers to structural modifications which negatively affect on the 5'-nuclease or FEN1 cleavage of the oligo- or polynucleotide incorporating these structural modifications. Examples of the 5'-nuclease-protecting modifications include, but not limited to minor groove binding tails (e.g. Afonina I. A., et al., 2002), PNA (e.g. Ortiz E., et al., 1998) and LNA monomers (e.g. Latorra D. et al., 2003; Di Giusto D. A. and King G. C., 2004), can be very effective in design of the CD-ODNs.

"Hybridizing," "hybridization" or "annealing" refers to a process of interaction between two or more oligo- and/or polynucleotides forming a complementary complex through base pairing which is most commonly a duplex or double stranded complex as originally described in Doty P. et al (1960). The stability of a nucleic acid duplex is measured by the melting temperature, or "Tm". "Melting temperature" or "Tm" means the temperature at which a complementary complex of nucleic acids, usually double-stranded, becomes half dissociated into single strands. These terms are also used in describing stabilities of polynucleotide secondary structures wherein two or more fragments of the same polynucleotide interact in a complementary fashion with each other forming complexes, usually hairpin-like structures. The term "binding site" refers herein to a sequence within an oligo or polynucleotide to which another oligonucleotide is completely or partially complementary.

"Hybridization properties" of a polynucleotide means an ability of this polynucleotide or its fragment to form a sequence specific complex with another complementary polynucleotide or its fragment. "Hybridization properties" is also used herein as a general term in describing the complementary complex stability. In this aspect, "hybridization properties" are similar in use to yet another term, "melting temperature" or "Tm." "Improved" or "enhanced hybridization properties" of a polynucleotide refers to an increase in stability of a complex of this polynucleotide with its complementary sequence due to any means including but not limited to a change in reaction conditions such as pH, salt concentration and composition, for example, an increase in magnesium ion concentration, presence of complex stabilizing agents such as intercalators or minor groove binders, etc., conjugated or not. The hybridization properties of a polynucleotide or oligonucleotide can also be altered by an increase or decrease in polynucleotide or oligonucleotide length. The cause of the hybridization property enhancement is generally defined herein in context.

The term "label" refers to any atom or molecule that can be used to provide a detectable signal and that can be attached to a nucleic acid or oligonucleotide. Labels include but are not limited to isotopes, radiolabels such as $^{32}P$; binding moieties such as biotin; haptens such as digoxgenin; luminogenic, mass tags, phosphorescent or fluorescent moieties, fluorescent dyes alone or in combination with other dyes or moieties that can suppress or shift emission spectra by FRET effect. Labels may provide signals detectable by fluorescence, radioactivity, colorimetry, gravimetry, X-ray diffraction or absorption, magnetism, enzymatic activity, mass spectrometry, binding affinity and the like. A label may be a charged moiety or alternatively, may be charge neutral. Labels can include or consist of nucleic acid or protein sequence, so long as the sequence comprising the label is detectable. The term "FRET-labeled" refers a probe which usually incorporates two dyes that are in a FRET interaction.

"Fluorescent label" refers to a label that provides fluorescent signal. A fluorescent label is commonly a fluorescent dye, but it may be any molecule including but not limited to a macromolecule like protein, or a particle made from inorganic material like quantum dots, as described in (Robelek R. et al, 2004).

"FRET" is an abbreviation of Förster Resonance Energy Transfer effect. FRET is a distance-dependent interaction occurring between two dye molecules in which excitation is transferred from a donor to an acceptor fluorophore through dipole-dipole interaction without the emission of a photon. As a result, the donor molecule fluorescence is quenched, and the acceptor molecule becomes excited. The efficiency of FRET depends on spectral properties, relative orientation and distance between the donor and acceptor chromophores (Förster T., 1965). As used herein, "FRET probe" refers to a fluorescent oligonucleotide which is used for detection of a nucleic acid of interest wherein detection is based on FRET effect.

A "reaction mixture" generally means a solution containing all the necessary reactants for performing an amplification or detection reaction or both.

The term "reaction vessel" refers to any kind of a container used to perform the amplification and/or detection reactions of the methods of the invention and wherein the term "reaction vessel" means any appropriate way of isolation of the reaction mixture from the environment.

As used herein, the term "kit" refers to any system for delivering materials. In the context of reaction assays, such delivery systems include elements allowing the storage, transport, or delivery of reaction components such as oligonucleotides, buffering components, additives, reaction enhancers, enzymes and the like in the appropriate containers from one location to another commonly provided with written instructions for performing the assay. Kits may include one or more enclosures or boxes containing the relevant reaction reagents and supporting materials. The kit may comprise two or more separate containers wherein each of those containers includes a portion of the total kit components. The containers may be delivered to the intended recipient together or separately.

The term "solid support" refers to any material that provides a solid structure with which another material can be attached. Such materials may include but not limited to silicon, plastic, metal, glass, ceramic surfaces, and the like. Solid supports may be of a rigid or non-rigid nature like gels, rubbers, polymers, etc. and may be any type of shape including spherical shapes like beads. Certain embodiments of the present invention have at least one of the reaction components such as, e.g. primer, amplicon, cleavage-directing oligonucleotide or probe, immobilized on solid support at amplifying or detecting stages or both. A biological material is "immobilized" to a solid support when it is associated with the solid support through a random or non-random chemical or physical interaction. The immobilization or attachment may be through a covalent bond using specialty spacer molecule or linker group. However, the immobilization need not be covalent or permanent.

As used herein, "detection assay" or "assay" refers a reaction or chain of reactions that are performed to detect nucleic acids of interest. The assay may comprise multiple stages including amplification/enrichment and detection reactions performed consequently or in real time, nucleic acid isolation and intermediate purification stages, immobilization, labeling, etc. The terms "detection assay" or "assay" encompass a variety of derivative forms of the methods of the invention, including but not limited to, a "post-amplification assay" when the detection is performed after the amplification stage, a "real time assay" when the amplification/enrichment and detection are performed simultaneously, a "FRET assay" when the detection is based using FRET effect, "immobilized assay" when one of either amplification, enrichment or detection oligonucleotide components or an amplification product is immobilized on solid support, and the like.

In general, the term "design" in the context of the methods and/or oligonucleotides, etc., has broad meaning and in certain respects is equivalent to the term "selection". For example, the terms "oligonucleotide design", "primer design", "probe design" can mean or encompass selection of a particular, or sometimes not necessarily to a particular, oligonucleotide structure including the nucleotide sequence and structural modifications (e.g., labels, modified nucleotides, linkers, etc.). The term "system design" generally incorporates the terms "oligonucleotide design", "primer design", "probe design" and also refers to relative orientation and/or location of the oligonucleotide components and/or their binding sites within the target nucleic acids. In these aspects, the term "assay design" relates to the selection of any, sometimes not necessarily to a particular, methods including all reaction conditions (e.g. temperature, salt, pH, enzymes, oligonucleotide component concentrations, etc.), structural parameters (e.g. length and position of primers and probes, design of specialty sequences, etc.) and assay derivative forms (e.g. post-amplification, real time, immobilized, FRET detection schemes, etc.) chosen to amplify and/or to detect the nucleic acids of interest.

Description of Exemplary Aspects:

Present invention relates to the methods that enable enrichment of a target nucleic acid in a mixture of homologous sequences during amplification. Unlike many conventional assays, methods of the present invention allow to combine amplification, target enrichment and the target detection which may be performed in real time. The invention can be practiced in a variety of derivative forms to expand and to improve the nucleic acid detection capabilities in detection of rare polymorphic variation for forensics, environmental testing, clinical diagnostics, etc. Methods of the invention are in particular useful for epigenetic testing and cancer diagnostics. The inventive aspects benefit nucleic acid detection in many ways, for example, by reducing the time of the assay, simplifying and accelerating the detection, saving time on the assay development, increasing the assay sensitivity and specificity of action, improving the assay multiplexing capabilities, etc.

The methods of the invention are capable to enrich a target nucleic acid in a reaction mixture with one or more homologous nucleic acids during amplification wherein the target enrichment is provided by cleavage of the homologous nucleic acids using a FEN1 activity. In particular, the methods of the invention comprise a target nucleic acid and at least one another nucleic acid that is homologous to the target nucleic acid but different from the target nucleic acid by at least one nucleotide; at least one cleavage-directing oligonucleotide which binding site to said target nucleic acid and said homologous nucleic acid incorporates the sequence variation; a DNA polymerase activity; a FEN1 activity; one or more amplification primers, deoxynucleoside 5'-triphosphates and other reagents suitable to support the amplification of both nucleic acids incorporating the sequence variation; and performing the amplification reaction under reaction conditions suitable to support hybridization of the cleavage-directing oligonucleotide to the homologous nucleic acid providing the cleavage of the homologous nucleic acid and its amplification products in presence of the FEN1 activity and resulting in preferential amplification of the target nucleic acid and increase in amounts of the target nucleic acids relative the amounts of the homologous nucleic acid during the amplification.

Methods of the invention may be applied to enrich the target nucleic acids in a mixture of homologous nucleic acids using various amplification reactions which are not sensitive to presence of the FEN1 activity during amplification. The methods may be used in the isothermal amplification reactions. Examples of these amplification schemes include but not limited to Helicase-Dependant Amplification (HAD) (e.g. Vincent M. et al, 2004; An L. et al., 2005), Rolling Circle amplification (RCA) (Lizardi P., 1998; Baner J. et al., 1998) and Nucleic Acid Sequence-Based Amplification (NASBA) (Oehlenschlager F. et al (1996); Davey C. and Malek L. T., 2000). In preferred embodiments, the target enrichment is performed during PCR (e.g., U.S. Pat. Nos. 4,683,195 and 4,683,202 to Mullis K. B.).

Figure 2:
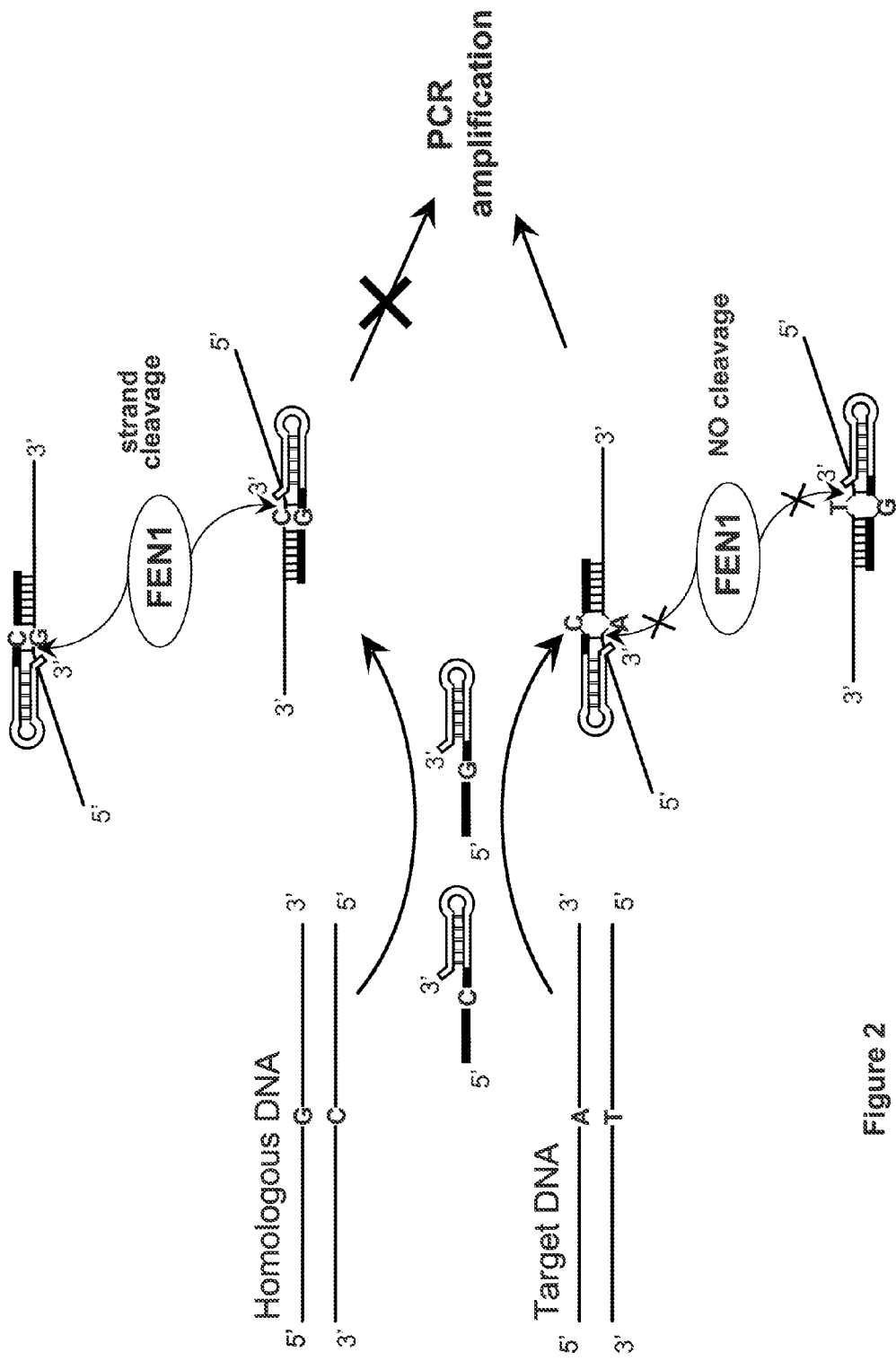
FIG. 2 illustrates, according to particular exemplary aspects of the present invention, a method of enrichment of a SNP target A/T allele during PCR amplification in presence of a homologous G/C gene sequence. The method shown is based on the use of two cleavage-directing oligonucleotides (CD-ODNs), each of which is complementary to the corresponding strand of the duplex DNA produced during PCR.
Figure 3:
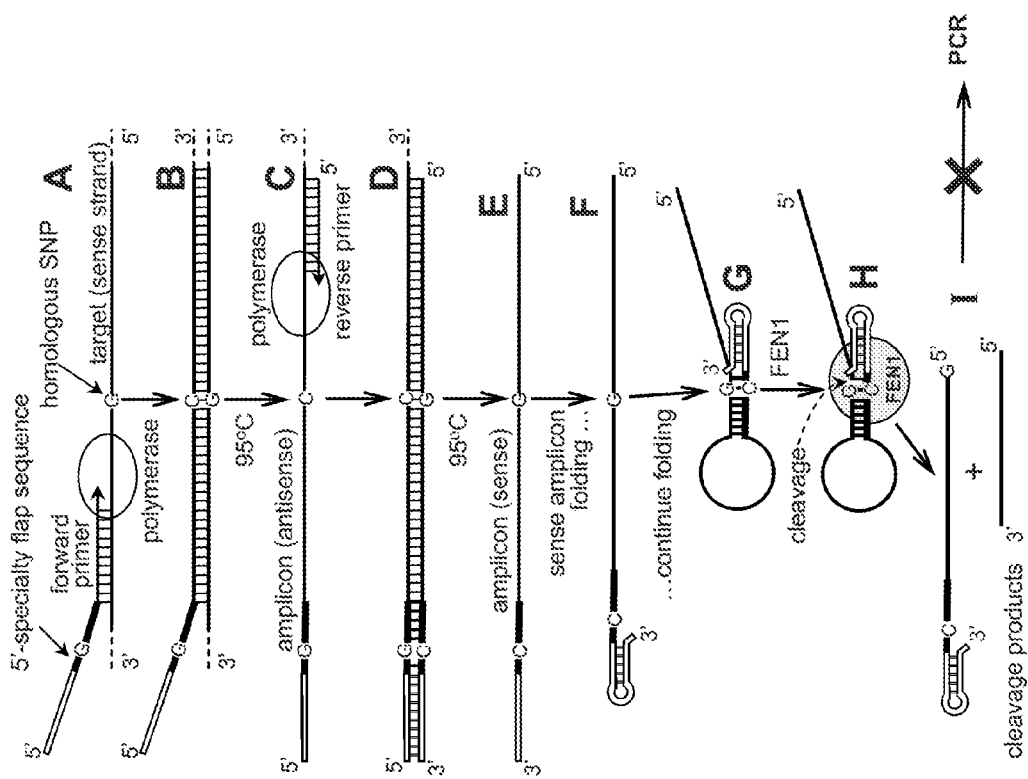
FIG. 3 shows, according to particular exemplary aspects of the present invention, a PCR-based method wherein a cleavage-directing oligonucleotide is formed at the 3'-end of an amplicon.

In methods of the invention, the homologous sequences are cleaved during the amplification and therefore are not effectively amplified whereas the nucleic acids of interest escape the cleavage and amplify. The cleavage of the homologous sequence in presence of FEN1 endonuclease is initiated by a cleavage-directing oligonucleotide (CD-ODN) which binding site incorporates the polymorphic variation between the target and homologous sequences. Examples of the methods employing CD-ODNs to provide the selective cleavage of the homologous sequences are illustrated in FIGS. 2 and 3. The FEN1 endonuclease recognizes the complex of the CD-ODN with the homologous nucleic acid and cleaves the nucleic acid strand. In the shown examples of PCR-based amplification reactions, the cleavage takes place between the PCR primers or their binding sites and this reduces amount of the template during PCR slowing down the amplification. In case of the target nucleic acid, the CD-ODN forms a mismatched complex with the target nucleic acid and this negatively affects the cleavage efficiency. Thus, the target nucleic acid is efficiently amplified during PCR. The preferential amplification of the target nucleic acids in comparison with the homologous sequence results in enrichment of the target nucleic acid.

In one embodiment, the CD-ODN interacts exclusively with the products of the nucleic acids amplification. Example of this method based on PCR is illustrated in FIG. 3. The CD-ODN is synthesized during PCR and appears at the 3'-end of one of the amplicon strands of both, the target and homologous nucleic acids.

In another embodiment, the CD-ODN may interact with nucleic acids prior conducting the amplification. This approach, for example, can be applied in the methods of FIGS. 2 and 3 and provide for additional target enrichment.

DNA duplex comprises two complementary strands. In one embodiment, the CD-ODN is designed to interact with only one of the DNA strands. In preferred embodiments, two CD-ODNs are used and these CD-ODNs hybridize to the opposite amplicon strands. Cleavage of both amplicons of the homologous sequence is anticipated to increase the methods enrichment capabilities. Using the methods of the invention, the target nucleic acid can be enriched in presence of many homologous sequences. This would require the use of at least one CD-ODN designed for each of the homologous sequences to provide the cleavage of those homologous sequences during the amplification. Respectively, more than one target nucleic acid can be enriched in the same reaction mixture using at least one CD-ODN designed for each of the sequences that are homologous to those target nucleic acids. The methods of the invention are capable of the target nucleic acid enrichment of, at least, 100 times. In preferred embodiment, the level of the target enrichment is 1,000 times or greater. Ideally, the methods of the invention provide 1,000,000 times or greater enrichment of the target nucleic acid. Certain methods of the invention may have unlimited enrichment capabilities. For example, calculation show that in the exemplary experiment of FIG. 6 (left diagram in row C) the average PCR cycle yield of the homologous sequence amplification was roughly 5% in the case when two 5'-nuclease-protected CD-ODNs were applied (CD-ODN1-3 and CD-ODN2-3, FIG. 5). This correspondingly translates to 47.5% of average cleavage efficiency per a cycle and amplicon strand. The system is apparently short by 2.5% in the cleavage efficiency to completely stop the homologous sequence amplification.

Moreover, in the case when more than 50% of the cleavage efficiency is achieved, the reaction would enter into a deamplification process wherein the amounts of the homologous sequence begin to decrease during PCR.

The efficiency of the homologous sequence cleavage and target enrichment directly depends on the life time of the corresponding CD-ODN complex during the amplification. Therefore, the use of the 5'-CD-OND-modifications which either stabilize the CD-ODN duplex and, in certain embodiments, protect it from the 5'-nuclease cleavage, e.g. minor groove binding tails (e.g. Afonina I. A., et al., 2002), PNA (e.g. Ortiz E., et al., 1998) and LNA monomers (e.g. Latorra D. et al., 2003; Di Giusto D. A. and King G. C., 2004), can be very effective in design of the CD-ODNs for methods of FIG. 2. Both methods of FIGS. 2 and 3 may benefit using base-modified duplex-stabilizing dNTP analogs in the reaction mixture as described in Kutyavin, I. V. (2008). As shown and discussed in the FIG. 4 legend, the use of duplex-destabilizing template-efficient nucleotide analogs in the design of the primer flap sequences may promote the enrichment method of FIG. 3, especially when the amplification products for both strands are designed to provide self-cleavage.

Generally the sequence variation discriminating the target and homologous sequences in cleavage efficiency can be located anywhere within the target-specific sequence of CD-ODN (identified in FIG. 1). However, the preferred location is between the middle and 3'-end of the target-specific sequence. Appearance of mismatched nucleotides within the middle section of the target-specific sequence provides discrimination based on a "thermodynamic" factor wherein CD-ODN forms either stable (homologous sequence) or unstable (target sequence) duplexes. On the other hands, location of the sequence variation within approximately four nucleotides from the 3'-end of the target-specific sequence may elaborate the discrimination implicating the FEN1 enzymatic activity which is known to be sensitive to the mismatches located in this duplex region.

The DNA polymerase and flap endonuclease activities required for the enrichment assays may be provided by the same or independent enzymes. For example, Taq DNA polymerase from *Thermus aquaticus* comprises two polypeptide domains (Lawyer F. C. et al., 1993). One domain expresses DNA polymerase activity whereas another domain is a duplex-specific 5'-nuclease (FEN1 activity). This enzyme carries two enzymatic activities and can be used in methods of FIGS. 2 and 3. The presence of both activities in the same protein may be beneficial in some aspects of the invention. However, the DNA synthesis and cleavage are separated in time and in space, i.e. occur in different complexes. In certain embodiment, the key catalytic activities are provided by independent proteins. For example, lack of the 5'-nuclease in DNA polymerase may help to avoid digestion of the cleavage-directing ODNs in the method of FIG. 2 (TaqMan mechanism). This, in turn, may extend the lifetime of the optimal cleavage structure shown in FIGS. 1 and 2.

The target DNAs enriched by the methods of the invention can be used for variety of purposes including, for example, sequencing. Detection of nucleic acids is an important application of the invention. In preferred embodiment, target nucleic acid is enriched and then detected using one of post-amplification and real time methods. The methods of the invention can be used to measure the amount of the target nucleic acid in the sample. The reactions can be conducted using "micro arrays" format wherein at least one of the primers, amplicon strands and CD-ODN is immobilized on a solid support during the amplification and target enrichment. In the detection assays, an oligonucleotide probe may be also immobilized.

There are many approaches known in the Art to detect nucleic acids. In preferred aspects, the target nucleic acid is detected using oligonucleotide probe. Nucleic acids can be detected at nanomolar level using fluorescence labels and this is well within PCR productivity. In preferred embodiment, the oligonucleotide probe is fluorescently labeled. Fluorescent detection of a PCR amplicon commonly employs the Förster Resonance Energy Transfer (FRET) effect. FRET is a distance-dependent interaction occurring between two dye molecules in which excitation is transferred from a donor to an acceptor fluorophore through dipole-dipole interaction without the emission of a photon. As a result, the donor molecule's fluorescence is quenched, and the acceptor molecule becomes excited. The efficiency of FRET depends on spectral properties and the relative orientation and distance between the donor and acceptor chromophores (Förster T., 1965). In the case of random dipole orientation and a good overlap between the emission spectrum of the donor and the absorption spectrum of the acceptor, the efficiency of FRET is dependent on the inverse sixth power of the intermolecular separation (Förster T., 1965). This makes FRET useful over distances comparable to the dimensions of biological macromolecules (Stryer, L., Haugland, R. P., 1967). As a reporter method, FRET is widely used in biomedical research and particularly in probe designs for nucleic acid detection (Didenko V. V., 2001). The acceptor chromophore is usually a non-fluorescent dye chosen to quench fluorescence of the reporting fluorophore (Eftink M. R., 1991). The oligonucleotide probes of the invention are preferably FRET probes.

The FRET probes of the invention can be hybridization-triggered or cleavable probes. Examples hybridization-triggered probes include but not limited to Adjacent Hybridization probes (Cardullo R. A., et al., 1988; Gundry C. N., et al., 1999), Self-Quenching Fluorescence probes (Livak K. J., et al., 1998), Molecular Beacons (Tyagi S. and Kramer F. R., 1996; Bonnet G., et al., 1999), Scorpion primers (Whitcombe D., et al., 1999; Thelwell N., et al., 2000), Eclipse probes (Afonina I. A., et al., 2002) incorporating a 5'-conjugated minor groove binding moiety (MGB) (Kutyavin I. V., et al., 1997). The FRET probes of the invention are preferably cleavable probes. In preferred aspects, the FRET probes are cleaved by a flap endonuclease activity. Examples of the FRET probes that are cleaved by FEN1 include Taqman (Gelfand D. H., et al., 1993), Snake (Kutyavin I. V., 2010) and other system designs (Kutyavin I., 2007). The Snake technology is a preferred nucleic acids detection system to be used in the methods of the invention. In particular, this method can be effectively combined with the enrichment method of FIG. 3.

Additional embodiment includes a kit to perform the methods of the invention wherein the kit comprises a pair of primers and sequence-discriminating oligonucleotide for every target nucleic acid to be enriched and amplify. In yet another additional embodiment, the kit further comprises an oligonucleotide probe.

Key Reaction Components:

A. Target Nucleic Acids.

In the target enrichment methods of the invention, the nucleic acids of interest and its homologous sequences can be of any nature, e.g. DNA, RNA or DNA/RNA hybrids, any sequence, structure or shape, e.g. linear or circular, single stranded or double stranded. For example, when the target nucleic acid is RNA, it can be converted prior to PCR to DNA/RNA heteroduplexes or to duplex cDNA by known methods in the Art, e.g. described in Simpson D. et al (1988) and Belyaysky A. et al (1989) and the like. These methods employ a reverse transcriptase activity of certain DNA polymerase that can extend an oligonucleotide primer hybridized to a RNA template providing synthesis of complementary DNA (cDNA) in presence of deoxynucleoside 5'-triphosphates (dNTPs). Regarding the PCR-based detection assays, the methods are well known in the art under the names "reverse transcription PCR" or "RT-PCR" as described in Tecott L. et al (1992), which patent is incorporated herein by reference.

Those of ordinary skill in the art will appreciate that the target nucleic acids should be sufficiently free of proteins and other substances interfering with the amplification process. Many methods are available for the isolation and purification of nucleic acids of interest including commercial kits and specialty instruments. Examples of these methods can be found in Ausubel et al., (1993); Walsh et al. (1991); Miller et al (1988).

B. Oligonucleotide Components.

The oligonucleotide components of the invention such as oligonucleotide primers, cleavage-directing oligonucleotides and probes may be synthesized using techniques that are well known in the Art. Oligonucleotide components can be prepared by any suitable method of chemical synthesis. The preferred approach is the diethylphosphoramidate method disclosed in Beaucage S. L. and Caruthers M. H. (1981) in combination with the solid support method disclosed in Caruthers M. H., Matteucci M. D. (1984) and performed using one of commercial automated oligonucleotide synthesizer. When probes of the invention need to be labeled with a fluorescent dye, a wide range of fluorophores may be applied. Available fluorophores include but not limited to coumarin, fluorescein (FAM, usually 6-fluorescein or 6-FAM), tetrachlorofluorescein (TET), hexachloro fluorescein (HEX), rhodamine, tetramethyl-rhodamine, BODIPY, Cy3, Cy5, Cy7, Texas red, ROX and other dyes. FRET probes of the invention commonly incorporate a pair of fluorophores, one of which may be a none-fluorescent chromophore (commonly referred as a "dark quencher"). Suitable dark quenchers described in the Art include Dabcyl and its derivatives like Methyl Red. Commercial nonefluorescent quenchers, e.g. Eclipse (Glen Research) and BHQ1, BHQ2, BHQ3 (Biosearch Technologies), may be also used for synthesis of FRET probes of the invention.

Figure 4:
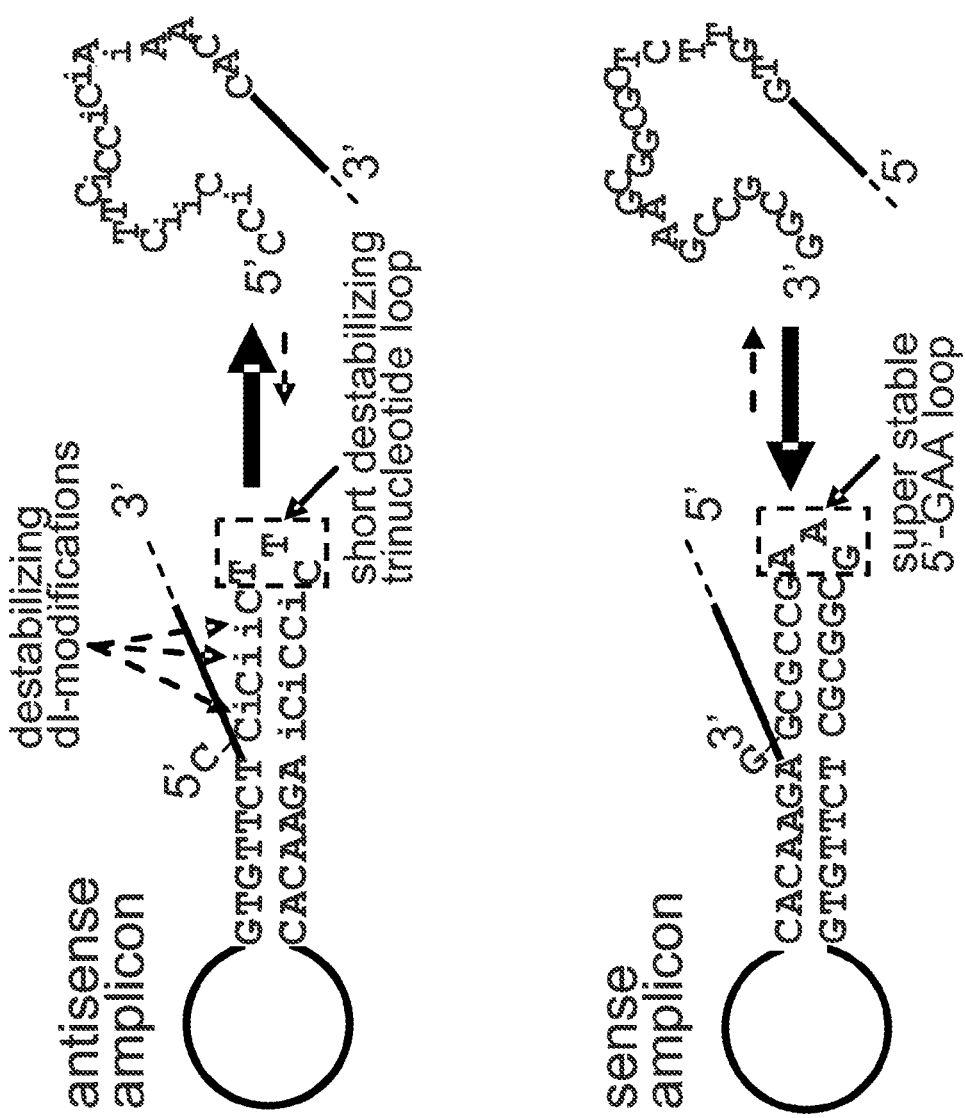
FIG. 4 illustrates, according to particular exemplary aspects of the present invention, an approach to discriminate in stability the 5'- and 3'-secondary structures in antisense (SEQ ID NO:1) and sense (SEQ ID NO:2) amplicons of the method of FIG. 3.

Oligonucleotide components of the invention may contain structural modifications other than fluorescent dyes and linkers, e.g. different moieties, residues and nucleotide analogs which are usually of a synthetic nature and which are not commonly present in natural nucleic acids. Modified nucleoside or nucleotide analogs which rarely present in natural nucleic acid may be incorporated synthetically into oligonucleotide components, for example, inosine (hypoxanthine), 5-bromouracil, 5-methylcytosine, 5-iodouracil, 2-aminoadenosine and the like. Duplex-stabilizing modifications are preferred structural modifications because, in general, use of these modifications allow to reduce the length of oligonucleotide components or, alternatively, to use more stringent amplification conditions providing better target enrichment results. Those of ordinary skill in the Art will appreciate that there are certain rules and limits in use of the structural modifications which depend on many factors characteristic to particular methods of the invention including the oligonucleotide component functional activity. For example, the methods of FIG. 2 may benefit using CD-ODNs incorporating duplex-stabilizing and/or 5-nuclease protecting modifications like, e.g. minor groove binding tails (e.g. Afonina I. A., et al., 2002), PNA (e.g. Ortiz E., et al., 1998) and LNA monomers (e.g. Latorra D. et al., 2003; Di Giusto D. A. and King G. C., 2004) at their 5'-end. However, use of certain structural modifications nearby the 3'-end of the target-specific sequence (FIG. 1) should be avoided because the modifications may interfere with the FEN1 activity. Methods of FIG. 3 are very limited in structural modifications which can be introduced into CD-ODNs because these oligonucleotide components are synthesized during the amplification. However, as illustrated in FIG. 4, the methods of FIG. 3 may benefit using duplex-destabilizing polymerase-efficient nucleoside modifications in design of the specialty flap sequences. Many of the structural modifications useful in practicing the methods are available from commercial sources, e.g. Glen Research, Integrated DNA Technologies, and others.

There are certain common requirements to the oligonucleotide components, for example, the hybridization properties of the oligonucleotides need to address the temperature of a particular reaction, usually referred as melting temperature (Tm). Tm defines a temperature at which a complementary complex of an oligonucleotide component with target nucleic acid becomes half dissociated into single strands. A simple estimate of the Tm value may be calculated using the equation Tm=81.5+0.41 (% G+C), when a nucleic acid is in aqueous solution at 1 M NaCl. More accurate calculations can be made using the base pair thermodynamics of a "nearest-neighbors" approach (Breslauer K J. et al, 1986; SantaLucia J. Jr., 1998). Commercial programs, including Oligo™, Primer Design and programs available on the internet, including Primer3 and Oligo Calculator can be also used to calculate a Tm of a nucleic acid sequence useful according to the invention. Melting temperatures of secondary structures may be determined using approach and algorithm described in e.g. Zuker M. and Jacobsen A. B. (1995).

C. Cleavage-Directing Oligonucleotides.

The cleavage directing oligonucleotides of the invention comprise a target-specific sequence and a duplex with a 3'-mismatched nucleotide. An example of the cleavage-directing oligonucleotide is schematically shown in FIG. 1. FIG. 1 illustrates an exemplary system design which enables cleavage of a single-stranded DNA at any nucleotide position using a cleavage-directing oligonucleotide. The FEN1 nuclease substrate in this design is a simulated or pseudo nicked double-stranded DNA. In the optimal cleavage substrate, the duplexes on each side of the nick are in coaxial stacking with no unpaired nucleotides between them. Appearance of the unpaired nucleotides between the duplexes negatively affects the FEN1 cleavage. Both 5' and 3'-ends of the DNA strand at the site of the nick may or may not have flap-sequences. The 5'-flap sequence can be of any length whereas the 3'-flap sequence is preferably not longer than one nucleotide, where longer 3'-flap sequences reduce the FEN1 cleavage efficiency. In the shown preferred example, the cleavage-directing oligonucleotide is a hairpin-shaped single molecule comprising a duplexed segment and a single-stranded target-specific sequence. As shown in this FIG. 1, hybridization of this target-specific sequence to its complementary site within the single-stranded DNA simulates the formation of an optimal cleavage structure for FEN1 nuclease. The nuclease recognizes the substrate and cleaves the single-stranded DNA strand as indicated. The purpose of the 3'-terminal mismatched nucleotide, i.e. the single nucleotide 3'-flap, is to prevent the 3'-end from extension by DNA polymerase. This 3'-terminal nucleoside may be absent, i.e. the 3'-end is carrying a phosphate moiety, or replaced with a small non-extendable moiety like 1,3-propane diol. FEN1s are highly selective enzymes and appearance of a mismatch within the base pairs shown in the box is anticipated to block the cleavage.

FIG. 2 illustrates, according to particular exemplary aspects of the present invention, a method of enrichment of a SNP target A/T allele during PCR amplification in presence of a homologous G/C gene sequence. The method shown is based on the use of two cleavage-directing oligonucleotides (CD-ODNs), each of which is complementary to the corresponding strand of the duplex DNA produced during PCR. Hybridization of these CD-ODNs to the homologous DNA strands leads to the formation of optimal cleavage structures that are recognized and cleaved by an FEN1 nuclease. The cleavage takes place between PCR primers sites and therefore the homologous DNA is not amplified. In the case of the target allele, the FEN1 cleavage is blocked due to the A-C and T-G mismatches at the nuclease sites, providing no negative effect on the PCR amplification. Shown is the ideal situation wherein the FEN1 cleavage efficiency of the homologous sequence is 100% while the target sequence is not cleaved. In the case of partial strand cleavage, the homologous sequence would be amplified but at a slower rate.

In the methods of FIG. 2, the duplex fragment may be created by using two oligonucleotides. In preferred embodiments, CD-ODNs are single molecules having the 3'-sequence fragments to fold into the secondary structures. The purpose of the 3'-terminal mismatched nucleotide is to prevent the 3'-end from extension by DNA polymerase during the amplification. In the methods of FIG. 2, this 3'-terminal nucleoside may be absent, i.e. the 3'-end is carrying a phosphate moiety, or replaced with a small non-extendable residue like, e.g. 1,3-propane diol. The 3'-duplex fragment of CD-ODNs can be generally of any length but preferably not shorter than tetranucleotide. In preferred aspects, the nucleotide composition (A/T and G/C base pairs) and the duplex length are selected to provide a stable complex during the amplification and target enrichment.

The target-specific sequence of CD-ODN is defined by the sequence of the homologous and target nucleic acids and it incorporates the polymorphic variation between these nucleic acids. The complex of CD-ODN with the target has one or more mismatches according to the polymorphic variations. This complex may also have mismatches, other than those defined by the polymorphic variations, but in preferred embodiments these other mismatches are avoided in CD-ODN design, and the target-specific sequence of CD-ODN is fully complementary to the homologous sequence. The target-specific sequence may be of any length, but usually between 10 and 25 nucleotides. The length and the structural modifications within the CD-ODN target-specific sequence are selected to form a stable complex with the homologous sequence for its efficient cleavage, but do not block the amplification of the target nucleic acid. Regarding the cleavage efficiency and target enrichment, the PCR-based methods of the invention may have an advantage over the isothermal amplification technologies. As illustrated in the examples provided herein, the PCR cycle may comprise three steps: amplicon denaturation, a 'cleavage' step at a reduced temperature (e.g. 55-65° C.) and then a 'template-extension' stage at, e.g. 70-75° C. In this approach, CD-ODNs can be designed to form very stable complexes with the homologous sequence during the 'cleavage' step extending the life-time of the cleavage structure and resulting in the efficient cleavage of the homologous amplicons. The duplex stability of the hybridized cleavage-directing oligonucleotides may be as significant as it may block the replication of the target nucleic acid at the 'cleavage' step. However, the CD-ODNs complexes become unstable at the 'template-extension' step and allow the amplification to proceed replicating all amplicons including target and homologous, but the cleaved ones.

FIG. 3 shows, according to particular exemplary aspects of the present invention, a PCR-based method wherein a cleavage-directing oligonucleotide is formed at the 3'-end of an amplicon. A forward primer contains a 5'-flap sequence which is not immediately complementary to the amplified nucleic acid. A 5'-part of this flap sequence (white solid line) is an artificial sequence and serves to introduce a hairpin-like structure at the 3'-end of the complementary PCR amplicon. The rest of the flap (black solid line) is complementary to a DNA site located downstream from the primer binding site and incorporating a SNP homologous variation that, in contrast to the target SNP, needs to be inefficient in amplification. Extension of the forward primer in stage A results in the synthesis of an antisense strand, providing a double stranded amplicon (stage B). After strand separation (95° C.), a reverse primer hybridizes to the antisense strand and DNA polymerase extends the complex (stage C), resulting in yet another double-stranded amplicon (stage D). Since the 5'-flap of the forward primer functions as a template for DNA synthesis, a complement to this sequence appears at the 3'-end of a sense amplicon strand (also shown as solid line). After another round of strand separation, the sense amplicon (synthesized in stage D) starts folding into a secondary structure (stage F). Completion of the folding in stage G results in formation of the optimal cleavage structure for FEN1. In the case where the duplex strands perfectly match (homologous amplicon), the structure is recognized by a FEN1 nuclease and cleaved. Since the cleavage takes place between the primer binding sites, the resulting products do not participate in the exponential PCR amplification. In contrast, the target allele, e.g. G→A, would form an A-C mismatched structure, escape the FEN1-cleavage and amplify in PCR. Similar to the method shown in FIG. 2, in the method of FIG. 3 either one of two or preferably both PCR amplicons are designed for the sequence-specific "self-cleavage" and mutant enrichment.

Both methods of FIGS. 2 and 3 are based on the same principle wherein a cleavage-directing oligonucleotide hybridizes to a homologous nucleic acid and catalyzes it cleavage by a FEN1 nuclease. Due to the same principle, in both methods the cleavage can be addressed to one or both homologous amplicon strands. Regarding the design of CD-ODNs, the same general rules apply to both methods. However, certain differences in the methods' characteristics and capabilities can be underlined. For example, the method of FIG. 3 has a 'kinetic' advantage. Due to the intra-molecular amplicon folding, the cleavage structure in the method of FIG. 3 is formed almost 'instantly' compare to the method of FIG. 2 wherein it can take up to ~7-10 seconds to saturate the CD-ODN binding site. The faster the cleavage structure is formed, the greater the chances that the amplicon will be cleaved during the amplification. Due to the same intra-molecular folding, the target-specific sequences in CD-ODNs of FIG. 3 can be shorter than those in the method of FIG. 2. However, CD-ODNs of the FIG. 3 are more limited in the structural modifications which can be used.

FIG. 4 illustrates, according to particular exemplary aspects of the present invention, an approach to discriminate in stability the 5'- and 3'-secondary structures in antisense and sense amplicons of the method of FIG. 3. As shown in FIG. 3, the design of the system to provide a self-cleavable sense amplicon means that, due to the amplicons' complementarity, the antisense amplicon also folds into a similar secondary structure of the same stability but reverse 5'→3' orientation. In the methods of the invention, the sense amplicon folding is the desirable structure whereas the antisense one is not. The antisense folding can negatively affect the amplification as discussed in Kutyavin I. V. (2010). The antisense amplicon secondary structure can be destabilized using duplex-destabilizing template-efficient nucleotide analogs in the design of the primer flap sequences. As exemplified in FIG. 4, incorporation of deoxyinosine (shown as i) destabilizes the antisense amplicon folding shifting the equilibrium to the right. On the other hand, deoxyinosine is a template-efficient modification (Auer T., et al., 1996) and DNA polymerase incorporates deoxycytidine as it Watson-Crick counterpart during the DNA replication. Therefore, unlike the 5'-end structure of the antisense amplicon, the complementary 3'-end sense structure is not destabilized. Additional discrimination can be provided by design of the loop sequence. When the antisense structure incorporates a 3'- ... CTT ... -5' fragment between the duplex strands, this trinucleotide loop is too short and has no special properties in duplex stabilization. On the other hand, the complement to this sequence 5'- ... GAA ... -3' appears in the sense folding and, regardless of the short length, this GAA-loop represents the well known super-stabilizing loop-fragment (Hirao I., et al., 1992). Collectively, the application of duplex-destabilizing template-efficient nucleotide analogs in the primer flap sequences and the selection of the loop sequence illustrated in FIG. 4 make stable the desired sense amplicon folding, i.e. shifting the equilibrium to the left, whereas the 5'-end of the antisense amplicon remains unstructured and single-stranded.

Figure 5:
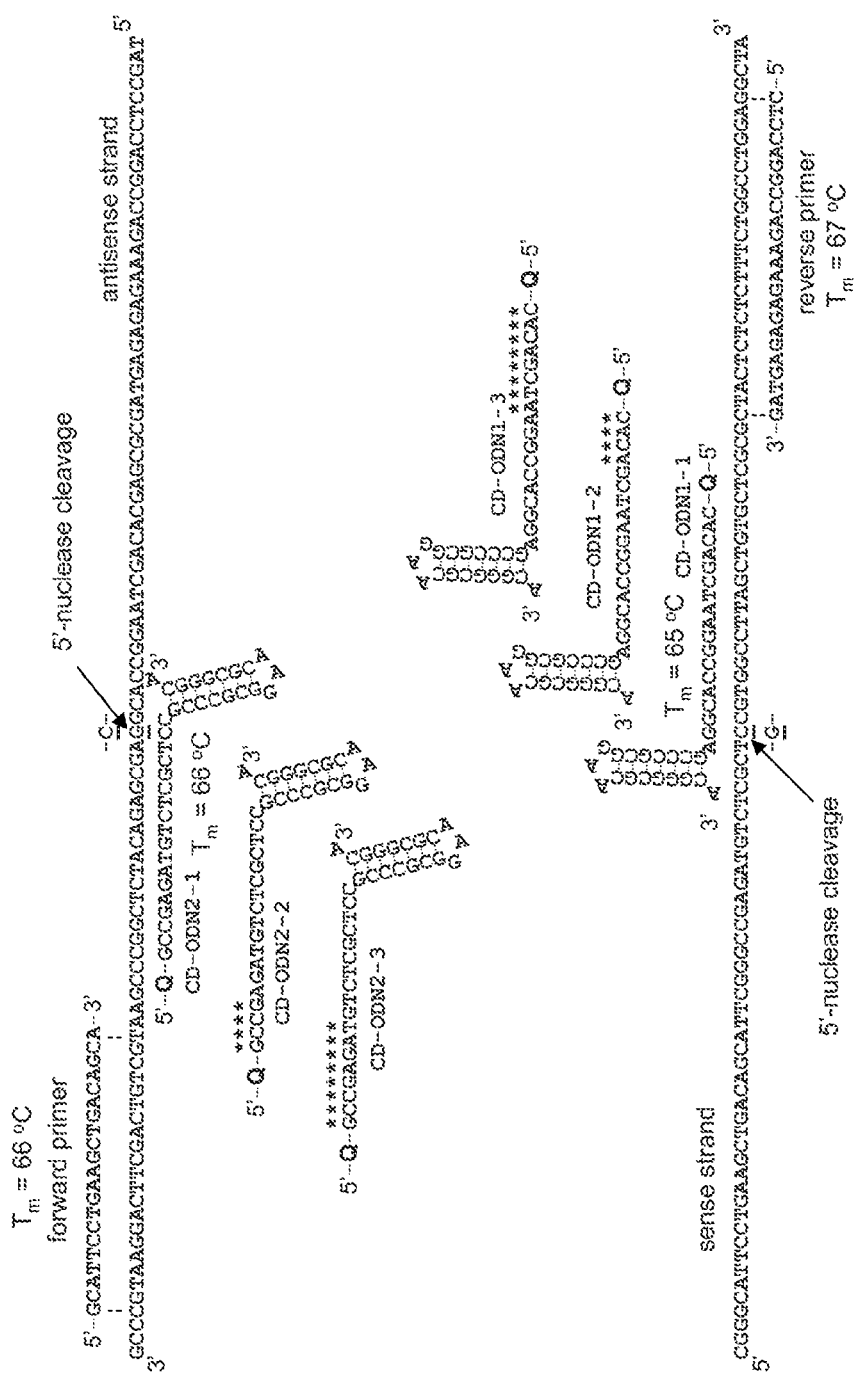
FIG. 5 shows the fragment of β2-microglobulin gene sequence (SEQ ID NO:4, antisense strand; SEQ ID NO:11, sense strand), the oligonucleotide primers (SEQ ID NO:3, forward primer; SEQ ID NO:12, reverse primer) and the cleavage-directing oligonucleotides (CD-ODNs) (CD-ODN1-1 (SEQ ID NO:10); CD-ODN1-2 (SEQ ID NO:9); CD-ODN1-3 (SEQ ID NO:8); CD-ODN2-1 (SEQ ID NO:5); CD-ODN2-2 (SEQ ID NO:6); and CD-ODN2-3 (SEQ ID NO:7) used in the exemplary enrichment experiment provided herein. Results of the target enrichment experiments using the oligo and polynucleotide components of FIG. 5 are shown in FIG. 6.

FIG. 5 shows the fragment of β2-microglobulin gene sequence (SEQ ID NO:4, antisense strand; SEQ ID NO:11, sense strand), the oligonucleotide primers (SEQ ID NO:3, forward primer; SEQ ID NO:12, reverse primer) and the cleavage-directing oligonucleotides (CD-ODNs) (CD-ODN1-1 (SEQ ID NO:10); CD-ODN1-2 (SEQ ID NO:9); CD-ODN1-3 (SEQ ID NO:8); CD-ODN2-1 (SEQ ID NO:5); CD-ODN2-2 (SEQ ID NO:6); and CD-ODN2-3 (SEQ ID NO:7) used in the exemplary enrichment experiment provided herein. Two synthetic 96-mer polynucleotides (sense strands) were used in the study, and the enrichment was performed during PCR. Shown are respectively sense (SEQ ID NO:11) and antisense (SEQ ID NO:4) strands of a homologous sequence with the SNP variation underlined. The target sequence was otherwise identical to the homologous one but incorporated a SNP variation indicated below and above of the sense and antisense strands, respectively. Wherever it is possible, the oligonucleotide sequences are aligned with the target DNA in the orientation (5'-to-3') as indicated. The cleavage-directing oligonucleotides CD-ODN1-1 (SEQ ID NO:10) and CD-ODN2-1 (SEQ ID NO:5) were prepared to catalyze the cleavage of the sense and antisense homologous strands. Q is a BHQ1 quencher (Biosearch Technologies) conjugated to the 5'-ends of CD-ODNs in an attempt to protect the cleavage-directing oligonucleotides from the 5'-hydrolysis by the Taq DNA polymerase during PCR. Each of these two CD-ODNs were also synthesized to incorporate four (CD-ODN1-2 (SEQ ID NO:9) and CD-ODN2-2 (SEQ ID NO:6)) or eight (CD-ODN1-3 (SEQ ID NO:8) and CD-ODN2-3 (SEQ ID NO:7)) 2'-O-methyl ribonucleotide analogs at the 5'-end as indicated by (*) sign. In these CD-ODN modified derivatives deoxyadenosine was correspondingly replaced using 2'-O-methyl riboadenosine analog, deoxythymidine with 2'-O-methyl ribothymidine, deoxycytidine with 5-methyl 2'-O-methyl ribocytidine and deoxyguanosine with 2'-O-methyl riboguanosine. Use of this modification aimed to protect CD-ODNs from the 5'-hydrolysis. The melting temperatures (Tm's) were calculated for a corresponding full complement duplex (200 nM) in 50 mM KCl, 5 mM $MgCl_2$, 20 mM Tris-HCl (pH 8.0). Results of the target enrichment experiments using the oligo and polynucleotide components of FIG. 5 are shown in FIG. 6.

Figure 6:
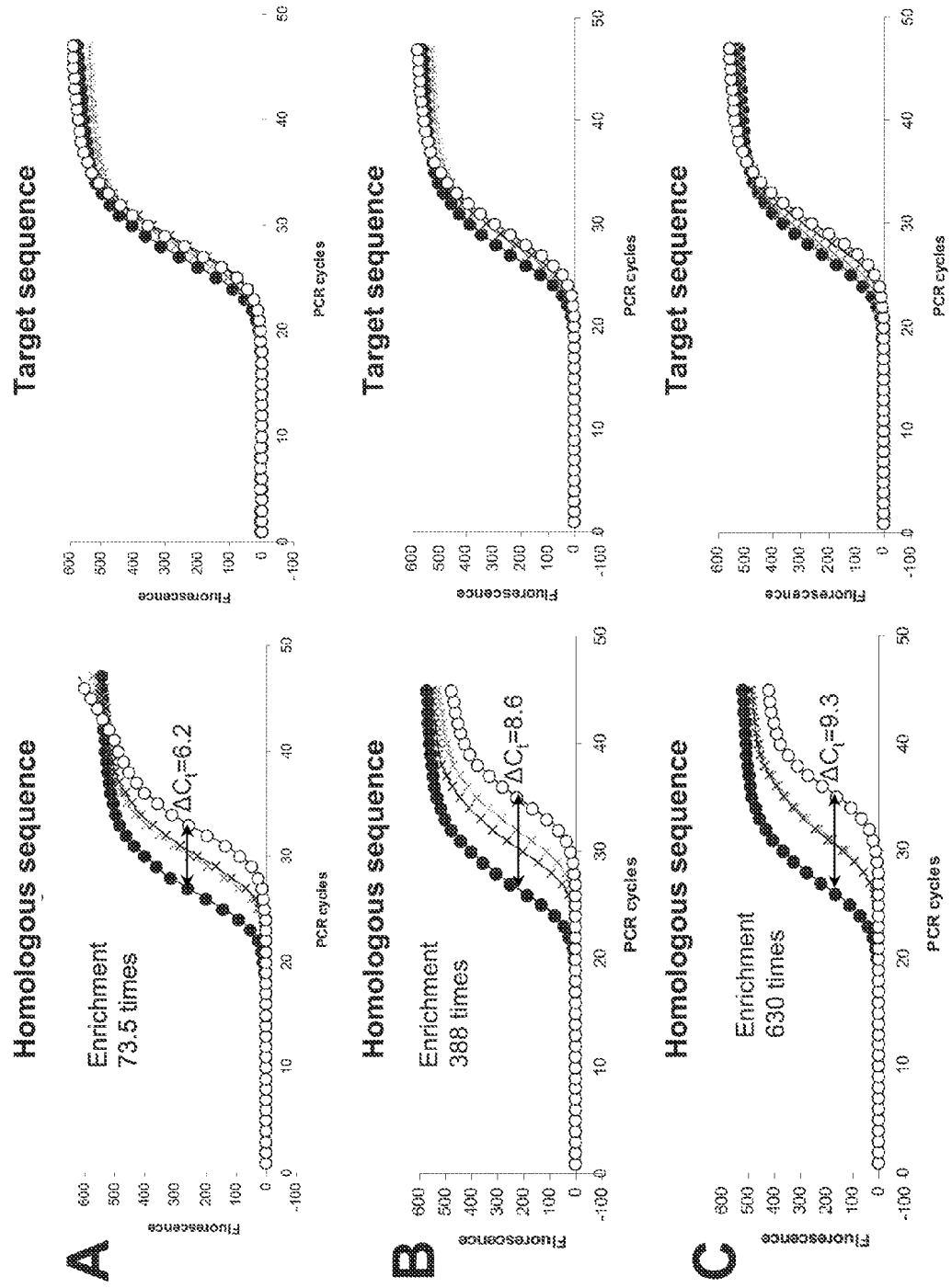
FIG. 6 shows, according to particular exemplary aspects of the present invention, results of the target DNA enrichment during PCR amplification. The diagrams are compiled in two columns (left and right) and three rows (A, B and C). Left column represents the enrichment and detection experiments performed with a homologous DNA whereas right column shows results of the same experiments but performed using a target nucleic acid. The three rows A, B and C show experiments performed using the cleavage-directing oligonucleotides CD-ODN1-1 and CD-ODN2-1 (row A), CD-ODN1-2 and CD-ODN2-2 (row B) and CD-ODN1-3 and CD-ODN2-3 (row C). The real time fluorescence curves marked by dark circles (•) represent 'control' experiments wherein the CD-ODNs were absent during the enrichment reaction. The curves marked by hollow circles (○) correspond to the experiments wherein both CD-ODNs directed to opposite amplicon strands were present in the enrichment reaction.

FIG. 6 shows, according to particular exemplary aspects of the present invention, results of the target DNA enrichment during PCR amplification. The diagrams are compiled in two columns (left and right) and three rows (A, B and C). Left column represents the enrichment and detection experiments performed with a homologous DNA whereas right column shows results of the same experiments but performed using a target nucleic acid. The three rows A, B and C show experiments performed using the cleavage-directing oligonucleotides CD-ODN1-1 and CD-ODN2-1 (row A), CD-ODN1-2 and CD-ODN2-2 (row B) and CD-ODN1-3 and CD-ODN2-3 (row C). The real time fluorescence curves marked by dark circles (•) represent 'control' experiments wherein the CD-ODNs were absent during the enrichment reaction. The curves marked by hollow circles (○) correspond to the experiments wherein both CD-ODNs directed to opposite amplicon strands were present in the enrichment reaction. The curves marked by (x) sign denote experiments wherein only one of the pair CD-ODNs were used in the enrichment reactions. Each of the shown curves is an average of four identical experiments. The experiments were conducted using two consecutive reactions, the enrichment and detection. First enrichment reaction comprised all necessary PCR components and either incorporated none (•), one of two (x) or both (○) CD-ODNs. After 10 PCR cycles, a sample of first reaction was used in the second detection reaction which did not include any CD-ODNs but contained EvaGreen® (Biotium) fluorescent dye to monitor the presence of the amplified nucleic acids in real time. Particularly the fluorescence curves obtained in this second reaction are shown in FIG. 6. The diagrams related to the experiments with the homologous sequence (left column) also show the differences in threshold values ($\Delta C_t$ in cycle number) between the cases when both CD-ODNs were present (○) and absent (•) in the enrichment reaction mixture. This value was used to calculate the PCR suppression factor (called 'Enrichment' in the diagrams). The calculation results are also indicated for all experiments in left column. Structure of all oligo and polynucleotides used in the experiments are shown in FIG. 5. The experimental details are provided in Examples of the Methods of the Invention.

D. DNA Polymerases.

DNA polymerases are key components in practicing nucleic acid assays of the present invention. DNA polymerases useful according to the invention may be native polymerases as well as polymerase mutants, which are commonly modified to improve certain performance characteristics or to eliminate 5' to 3' and/or 3' to 5' exo/endo nuclease activities that may be found in many native enzymes. Nucleic acid polymerases can possess different degrees of thermostability. To perform in PCR, DNA polymerase should be stable at temperatures>90° C., preferably >95° C. and even more preferably >100° C. Examples of thermostable DNA polymerases which are useful for performing the methods of the invention include but not limited to Pfu, Taq, Vent, Deep Vent and UlTma DNA polymerases and other polymerase from *Thermus* species or from *Ther-*

*motoga maritima*. DNA polymerases used in the methods of the invention may incorporate 5'→3' and 3'→5' "associated" nuclease activities. For example, Taq DNA polymerase from *Thermus aquaticus* has also duplex-specific 5'-nuclease or FEN1 activity and therefore this enzyme provides both activities that are necessary to practice the methods of the invention. JumpStart DNA polymerase from Sigma (antibody blocked Taq polymerase) was used in Examples provided herein. The DNA polymerases with the 3'→5' "proof-reading" activity should be avoided in the methods of FIG. 3, but can be used in the methods of FIG. 2, if the CD-ODNs are protected from the 3'→5' nuclease activity, for example, by thiophosphate modification of 3'-terminal nucleotides and/or conjugated moieties.

F. FEN1 Nucleases.

The duplex-specific 5'-nucleases or FEN1 nucleases are important components of the invention. These nucleases recognize the cleavage structure shown in FIG. 1 providing the cleavage of the homologous sequences and the enrichment of the target nucleic acids during the amplification. The FEN1 nucleases useful in practicing the invention do not substantially cleave either oligonucleotide probes or primers when they are in a single stranded state and when they are not hybridized to the target nucleic acids or amplification products. FEN1 activities useful in practicing the invention may be found in many DNA polymerases, e.g. *E. coli* DNA polymerase I and DNA polymerase isolated from *Thermus aquaticus* (Taq), *Thermus thermophilus* (Tth), *Pyrococcus furiosus* (Pfu) and *Thermus flavus* (Tfl). In certain embodiments of the invention, both assay activities, DNA polymerase and FEN1, are provided by the same enzyme, for example, Taq polymerase. Flap endonucleases have been identified in eukaryotes, prokaryotes, archea and viruses. Preferred FEN1 nucleases of the invention are thermophilic. However, methophilic 5'-endonucleases may be used in certain methods of the invention based on isothermal amplification.

Examples of the Methods of the Invention:

Sequences of the homologous and target 96-mer polynucleotide fragments and other oligonucleotide components used in the exemplary experiments are shown in FIG. 5. The primers and CD-ODNs were prepared according to standard procedures and laboratory techniques as described below.

Synthesis of Oligonucleotide Components.

Oligonucleotides were synthesized either on ABI394 DNA synthesizer (Applied Biosystems) or MerMaid 6 DNA synthesizer (Bio Automation Corporation) using protocols recommended by the manufacturers for 0.2 μmole synthesis scale. Standard phosphoramidites, 2'-O-methyl ribonucleoside phosphoramidites, solid supports and reagents to perform the solid support oligonucleotide synthesis were purchased from Glen Research. 5-Ethylthio-1H-tetrazile solution (0.25 M) was used as a coupling agent. The BHQ1 quencher (Q, FIG. 5) was purchased from Biosearch Technologies. After the automated synthesis, oligonucleotides were deprotected in aqueous 30% ammonia solution by incubation for 2 days at room temperature, 12 hours at 55° C. or 2 hours at 70° C.

Purification of Oligonucleotide Components.

Tri-ON oligonucleotide primers and 5'-BHQ1-tailed CD-ODNs were purified by HPLC on a reverse phase C18 column (LUNA 5 μm, 100 A, 250×4.6 mm, Phenomenex Inc) using gradient of acetonitryl in 0.1 M triethyl ammonium acetate (pH 8.0) or carbonate (pH 8.5) with flow rate of 1 ml/min. A gradient profile including washing stage 0→14%(10"), 14→45%(23'), 45→90%(10"), 90→90% (5'50"), 90→0%(30"), 0→0%(7'30") was be applied for purification of all Tri-ON and 5'-BHQ1-tailed oligonucleotides. The product containing fractions were dried down in vacuum (SPD 1010 SpeedVac system, TermoSavant) and trityl groups were removed by treatment in 80% aqueous acetic acid at room temperature for 40-60 minutes. After addition to the detritylation reaction (100 μl) of 20 μl sodium acetate (3 M), the oligonucleotides were precipitated in alcohol (1.5 ml), centrifuged, washed with alcohol and dried down. Concentration of the oligonucleotides was determined based on the optical density at 260 nm and the extinction coefficients calculated for individual oligonucleotides using on-line Oligo Analyzer 3.0 software provided by Integrated DNA Technologies. Based on the measurements, convenient stock solutions in water were prepared and stored at −20° C. for further use.

Oligonucleotide Quality Control and Tm Measurements.

Purity of all prepared oligonucleotide components was confirmed by ion-exchange and reverse phase HPLC and by spectroscopy on Cary 4000 UV-VIS spectrophotometer equipped with Cary WinUV software, Bio Package 3.0 (Varian, Inc.). $T_m$ calculations were performed in accordance with protocols described in Puglisi J. D. and Tinoco I, Jr. (1989) and Sugimoto N. et al (1996).

Target Enrichment PCR-Based Assay.

Evagreen® fluorescent dye was used to monitor the PCR amplification products in the experiment shown in FIG. 6. It was found that this dye negatively affects the amplicon cleavage in presence of CD-ODNs likely due to intercalation nearby the cleavage site in the amplicon-CD-ODN duplex. Therefore the enrichment experiments were conducted in two consequent reactions, first enrichment and then detection PCR.

Preparation of the Enrichment PCR Reactions.

Appropriate stock solutions of the reaction components were mixed at room temperature to provide the following concentration in 25 μL volume: the forward and reverse PCR primers—100 nM each; cleavage-directing ODNs (when present)—200 nM each; 96-mer DNA polynucleotide fragments (sense strands)—10,000 copies per reaction; dNTPs—200 μM each; heat-activated JumpStart DNA polymerase (Sigma)—0.2 U/μL in 50 mM KCl, 5 mM $MgCl_2$, 20 mM Tris-HCl (pH 8.0). The PCR enrichment reactions were performed using a 2720 Thermal Cycler instrument (Applied Biosystems) in 10 cycles comprising the incubation at 95° C. for 10 sec followed by a 'cleavage' stage at 56° C. for 45 sec and then a 'template-extension' stage at 72° C. for 30 sec. At the end of the enrichment PCR, the reaction were cooled dawn to 4° C., and a 1 μL sample of each reaction were used in the second detection PCR reaction. Use of the three-step PCR cycles in these experiments was important. CD-ODN can block the polymerase extension at the reduced temperature of the 'cleavage' stage. The enrichment methods of the invention are based on the amplicon cleavage and the 'physical' blockage of the DNA polymerase should be avoided. The use of the third 'template-extension' stage at 72° C. for 30 sec allows complete extension, i.e. replication, of all uncleaved amplicons, since the CD-ODN duplexes are unstable at this temperature while the PCR primers perform well.

Preparation of the Detection PCR Reactions.

A 1 μL sample of each enrichment reaction was mixed with appropriate stock solutions of the reaction components at room temperature to provide the following concentration in 100 μL volume: the forward and reverse PCR primers—200 nM each; EvaGreen® 0.2 U/μl; dNTPs—200 μM each; heat-activated JumpStart DNA polymerase (Sigma)—0.04 U/μL in 50 mM KCl, 5 mM $MgCl_2$, 20 mM Tris-HCl (pH 8.0). When all components were combined and mixed, the reaction was divided on four samples of 25 μL volume which underwent the detection PCR in parallel using a SmartCycler real time instrument (Cepheid). PCR was conducted in 47 cycles comprising the incubation at 95° C. for 10 sec followed by a combined 'annealing-extension' stage at 64° C. for 45 sec. Fluorescence of all four reaction samples was measured at the 'annealing-extension' stage. Each of the fluorescence curves (fluorescence vs. PCR cycle) shown in FIG. 6 represent an average of the four parallel experiments of the identical composition.

The purpose of the second PCR reaction was to assess the amounts of the polynucleotide material produced in the first enrichment reaction. The results shown in FIG. 6 (left column) indicate the suppression of the homologous sequence during PCR evidently caused by the cleavage of the amplified strands in presence of a single CD-ODN (curves marked by x). The effect of CD-ODNs appeared to be additive as the PCR suppression/cleavage more or less doubles in the case when both CD-ODNs were applied (curves marked by ○). In contrast to the experiments with the homologous sequence, the presence of CD-ODNs in the enrichment reaction had very little effect on the amplification of the target sequence (FIG. 6, right column) corroborating the proposed mechanism of the enrichment.

The efficiency of the homologous sequence cleavage directly depends on the life time of the CD-ODN complex with the complementary amplicon. The life time of this complex, in turn, depends on the ability of the Taq DNA polymerase to cleave and/or displace the CD-ODN oligonucleotides hybridized downstream from the primer-extension complex (Taqman mechanism). It was anticipated that the structural modifications at the 5'-end of a cleavage-directing oligonucleotide which protect the CD-ODN from the 5'-nuclease (FEN1) cleavage may be helpful to extend the life time of the CD-ODN complex promoting the homologous sequence cleavage and increasing the enrichment level. The 2'-O-methyl ribonucleotide analogs may be one of such modifications. Indeed, use of these sugar modifications led to increase of the $\Delta C_t$ values (FIG. 6, left column, rows B and C). Moreover, the efficiency of the homologous sequence suppression/cleavage during PCR intensifies with the increase in the number of the 5'-nucleotide modified from 0 to 4 and then to 8. In the best case of the cleavage-directing oligonucleotides CD-ODN1-3 and CD-ODN2-3 (left column, row C), the enrichment factor of 630 times was reached. Calculations show that, when the amplification is completely blocked within ten PCR cycles, the maximum theoretical enrichment factor is $2^{10}=1024$. Although the absolute enrichment was not reached in these exemplary experiments, there are ways to improve the CD-ODN-catalyzed template cleavage. The 2'-O-methyl modifications may be protecting the CD-ODNs from the 5'-nuclease cleavage by the Taq DNA polymerase, but this modification is known to have little, if any effect on the oligonucleotide hybridization properties. Thus the 2'-O-methyl-modified CD-ODNs are still prone to the displacement by DNA polymerase. In this aspect, the use of the 5'-CD-OND-modifications which either stabilize the CD-ODN duplex or protect it from the 5'-nuclease cleavage or preferably provide both properties, e.g. minor groove binding tails (e.g. Afonina I. A., et al., 2002), PNA (e.g. Ortiz E., et al., 1998) and LNA monomers (e.g. Latorra D. et al., 2003; Di Giusto D. A. and King G. C., 2004), can be very effective in design of the CD-ODNs.

REFERENCES CITED, AND INCORPORATED HEREIN BY REFERENCE THERETO FOR THEIR RESPECTIVE TEACHINGS

Afonina I. A., et al. (2002) *BioTechniques* 32: 940-949.
An L., et al. (2005) *JBC* 280: 28952-28958.
Auer T., et al. (1996) *Nucleic Acids Res.*, 24: 5021-5026.
Ausubel et al., (1993) eds., Current Protocols in Molecular Biology Vol. 1, Chapter 2, Section I, John Wiley & Sons, New York.
Baner J., et al. (1998) *Nucleic Acids Res.*, 26: 5073-5078.
Beaucage S. L., Caruthers M. H. (1981) *Tetrahedron Lett.* 22: 1859-1862
Belyaysky A. et al (1989) *Nucleic Acids Res.*, 17: 2919-2932
Bonnet G., et al. (1999) *Proc. Natl. Acad. Sci. USA* 96: 6171-6176.
Breslauer K J., et al (1986) *Proc. Natl. Acad. Sci. USA* 83: 3746-3750.
Brow M. A. D., et al. (1998) U.S. Pat. No. 5,846,717.
Cardullo R. A., et al. (1988) *Proc. Natl. Acad. Sci. USA* 85: 8790-8794.
Caruthers M. H., Matteucci M. D. (1984) U.S. Pat. No. 4,458,066.
Davey C. and Malek L. T. (2000) U.S. Pat. No. 6,063,603.
Didenko V. V. (2001) *BioTechniques* 31: 1106-1121.
Di Giusto D. A. and King G. C. (2004) *Nucleic Acids Res.* 32: e32.
Doty P., et al. (1960) *Proc. Natl. Acad. Sci. USA* 46: 461-476.
Eckstein F., ed., (1991) *Oligonucleotides and Analogs: A Practical Approach*. Oxford University Press, New York.
Eftink M. R. (1991) In Lakowicz, J. R. (ed.), *Topics in Fluorescence Spectroscopy*. Plenum Press, New York, V. 2, pp. 53-126.
Förster T. (1965) In Sinanoglu, O. (ed.), *Modern Quantum Chemistry, Istanbul Lectures, part III*. Academic Press, New York: 93-137.
Gait M. J., ed., (1984) *Oligonucleotide Synthesis: A Practical Approach*, IRL Practical Approach Series, IRL Press, Oxford.
Gelfand D. H., et al. (1993) U.S. Pat. No. 5,210,015.
Gocke C. D., et al. (2000) *Ann. N. Y. Acad. Sci.* 9906: 31-38.
Gundry C. N., et al. (1999) *Genet. Test.* 3: 365-370.
Hall J. G., et al. (1999) U.S. Pat. No. 5,994,069.
Hirao I., et al. (1992) *Nucleic Acids Res.*, 20: 3891-3896.
Kaur M., et al. (2002) *Mutagenesis* 17: 365-374.
Kornberg A., and Baker T. (1992) *DNA Replication*, Second Edition, W. H. Freeman and Company, New York.
Kutyavin I. V., et al. (1997) *Nucleic Acids Res.* 25: 3718-3723.
Kutyavin I. V. (2007) PCT application publication WO/2007/127999.
Kutyavin, I. V. (2008) *Biochemistry* 47: 13666-13673.
Kutyavin I. V. (2010) *Nucleic Acids Res.* 38: e29.
Jenkins G. J. S., et al. (1998) *Mutat. Res.* 405: 209-220.
Latorra D., et al. (2003) *Mol. Cell. Probes* 17:253-259.
Lawyer F. C., et al. (1993) *PCR Methods Appl.* 2: 275-287.
Lehninger A. L. (1975) *Biochemistry*, 2nd edition. New York, Worth Publishers, Inc.
Liu Q., Sommer S. S. (2000) *Biotechniques* 29: 1072-1083.
Livak K. J., et al. (1998) U.S. Pat. No. 5,723,591.
Lizardi P. (1998) U.S. Pat. No. 5,854,033.
Mackay I. M., et al. (2002) *Nucleic Acids Res.* 30: 1292-1305.
Mackay J., Landt O. (2007) *Methods Mol. Biol.* 353: 237-262.

McPherson M. J., et al., Eds (1991) *PCR: A Practical Approach*. IRL Press, Oxford.
McPherson M. J., et al., Eds (1995) *PCR2: A Practical Approach*. IRL Press, Oxford.
Milbury C. A., et al. (2009) *Clin. Chem.* 55: 632-640.
Miller et al (1988) *Nucleic Acids Res.,* 16: 1215.
Mullis K. B. (1987) U.S. Pat. No. 4,683,202.
Mullis K. B., et al. (1987) U.S. Pat. No. 4,683,195.
Oehlenschlager F., et al (1996) *Proc. Natl. Acad. Sci. USA,* 93: 12811-12816.
Ortiz E., et al. (1998) *Mol. Cell. Probes* 12:219-226.
Parry J. M., et al. (1990) *Mutagenesis* 5: 209-212.
Parsons B. L., Heflich R. H. (1997) *Mutat. Res.* 387: 97-121.
Prudent J. R., et al. (2000) U.S. Pat. No. 6,090,543.
Prudent J. R., et al. (1999) U.S. Pat. No. 5,985,557.
Puglisi J. D. and Tinoco L, Jr. (1989) *Methods Enzymol.* 180: 304-325.
Robelek R., et al. (2004) *Anal. Chem.* 76: 6160-6165.
Sambrook J., et al. (1989) *Molecular Cloning: A Laboratory Manual,* 2nd Edition. Cold Spring Harbor Lab. Cold Spring Harbor, N.Y.
SantaLucia J. Jr. (1998) *Proc. Natl. Acad. Sci. USA* 95: 1460-1465.
Shi J., et al. (2007) *Hum. Mutat.* 28: 131-136.
Simpson D. et al (1988) *Biochem. Biophys. Res. Commun.,* 151: 487-492
Stryer, L., Haugland, R. P. (1967) *Proc. Natl. Acad. Sci. USA* 58: 719-726.
Sugimoto N., et al (1996) *Nucleic Acids Res.* 24: 4501-4505.
Tecott L. et al (1992) U.S. Pat. No. 5,168,038.
Thelwell N., et al. (2000) *Nucleic Acids Res.* 28: 3752-3761.
Tyagi S. and Kramer F. R. (1996) *Nat. Biotechnol.* 14: 303-308.
Vincent M., Xu Y. and Kong H. (2004) *EMBO reports* 5: 795-800.
Walsh et al. (1991) *Biotechniques* 10: 506-513.
Whitcombe D., et al. (1999) *Nature Biotech.* 17: 804-807.
Zhou L. et al. (2010) *Clin. Chem.* 56: 814-822.
Zuker M. and Jacobsen A. B. (1995) *Nucleic Acids Res.* 23: 2791-2797.

The invention claimed is:

1. A method for enrichment during amplification of a target nucleic acid sequence in a mixture of target and homologous nucleic acid sequences, the method comprising:
   a) providing an amplification reaction mixture having a target nucleic acid sequence and at least one other nucleic acid sequence that is homologous to the target nucleic acid sequence but differs therefrom in at least one nucleotide position, at least one cleavage-directing oligonucleotide sequence, the respective binding sites of which to said target and to said homologous nucleic acid sequences include the at least one nucleotide position having the nucleotide sequence difference, a DNA polymerase activity, a FEN1 activity, one or more amplification primers, deoxynucleoside 5'-triphosphates and other reagents suitable to support the amplification of both target and homologous nucleic acid sequences; and b) amplifying the nucleic acids under reaction conditions suitable to support hybridization of the cleavage-directing oligonucleotide sequence to the homologous nucleic acid sequence providing for FEN1-mediated cleavage of the homologous nucleic acid and its amplification products, to provide for preferential amplification and increase in amount of the target nucleic acid sequence relative to that of the homologous nucleic acid sequence.

2. The method of claim 1, comprising, prior to amplifying, rendering the target nucleic acid and the at least one homologous nucleic acid single-stranded; and incubating the single-stranded target and homologous nucleic acids in the presence of the FEN1 activity and the at least one cleavage-directing oligonucleotide sequence under reaction conditions suitable to support hybridization of the cleavage-directing oligonucleotide sequence to the homologous nucleic acid sequence to provide for cleavage of the homologous nucleic acid by the FEN1 activity.

3. The method of claim 1, wherein two cleavage-directing oligonucleotide sequences are used, which hybridize to opposite strands of said homologous nucleic acid.

4. The method of claim 1, wherein the one or more amplification primers include a specialty 5' flap sequence that is complementary to the at least one cleavage-directing oligonucleotide sequence, and wherein the cleavage-directing oligonucleotide sequence is synthesized at the 3'-end of one or more amplification products of the target and homologous nucleic acids.

5. The method of claim 1, comprising use of a plurality of cleavage-directing nucleic acid sequences to provide for enrichment of a plurality of target nucleic acid sequences relative to a respective plurality of homologous nucleic acid sequences in the same reaction mixture.

6. The method of claim 1, wherein the cleavage-directing oligonucleotide sequence comprises, or is modified during amplification to include a duplex-stabilizing and/or a 5'-nuclease-protecting modification.

7. The method of claim 4, comprising incorporating at least one duplex-stabilizing nucleoside modification into the at least one cleavage-directing oligonucleotide sequence during amplification using a corresponding duplex-stabilizing base-modified deoxynucleoside 5'-triphosphate.

8. The method of claim 7, wherein the specialty 5' flap sequence comprises, or is modified during amplification to incorporate at least one duplex-destabilizing polymerase-efficient nucleoside modification.

9. The method of claim 1 providing for an enrichment of the target nucleic acid sequence, relative to the at least one homologous nucleic acid sequence, in the range of $10^3$ to $10^7$-fold.

10. The method of claim 1, wherein the FEN1 activity and the DNA polymerase activity are provided by the same enzyme.

11. The method of claim 1, wherein the target nucleic acid is detected using a post-amplification method and/or a real time method.

12. The method of claim 11, further comprising determining the amount of the target nucleic acid in the sample.

13. The method of claim 1, wherein at least one of the amplification primers, amplification products and cleavage-directing oligonucleotide sequence is immobilized on a solid support during the amplification and target enrichment.

14. The method of claim 1, wherein the amplification reaction comprises PCR.

15. The method of claim 1, wherein the amplification reaction comprises an isothermal amplification reaction.

16. The method of claim 11, wherein detecting the target nucleic acid comprises use of an oligonucleotide probe.

17. The method of claim 12, wherein detecting the target nucleic acid comprises use of an oligonucleotide probe.

18. The method of claim 17, wherein the oligonucleotide probe is fluorescently labeled.

19. The method of claim 18, wherein the oligonucleotide probe comprises a probe selected from the group consisting of a FRET probe, a cleavable FRET probe, and a FEN1-cleavable FRET probe.

20. The method of claim 19, wherein the probe detection method comprises a 5'-nuclease assay and/or a method comprising folding of PCR amplicons into secondary structures.

21. The method of claim 1, wherein the FEN1 activity and the DNA polymerase activity are provided by different enzymes.

* * * * *